US008445431B2

(12) United States Patent
Cowan et al.

(10) Patent No.: US 8,445,431 B2
(45) Date of Patent: May 21, 2013

(54) LIGANDS HAVING METAL BINDING ABILITY AND TARGETING PROPERTIES

(75) Inventors: James A. Cowan, Lewis Center, OH (US); Yan Jin, Columbus, OH (US); Seth Bradford, Columbus, OH (US); Nikhil Gokhale, Columbus, OH (US); Ada Cowan, Lewis Center, OH (US); Chun-An Chen, Powell, OH (US)

(73) Assignee: The Ohio State University, Columbus, OH (US)

( * ) Notice: Subject to any disclaimer, the term of this patent is extended or adjusted under 35 U.S.C. 154(b) by 1447 days.

(21) Appl. No.: 11/569,919

(22) PCT Filed: Jun. 1, 2005

(86) PCT No.: PCT/US2005/019288
§ 371 (c)(1),
(2), (4) Date: Apr. 4, 2008

(87) PCT Pub. No.: WO2005/117997
PCT Pub. Date: Dec. 15, 2005

(65) Prior Publication Data
US 2008/0188422 A1      Aug. 7, 2008

Related U.S. Application Data

(60) Provisional application No. 60/575,932, filed on Jun. 1, 2004.

(51) Int. Cl.
*A61P 31/18* (2006.01)
*A61K 38/03* (2006.01)

(52) U.S. Cl.
USPC .......................................... 514/3.8; 514/21.4

(58) Field of Classification Search
None
See application file for complete search history.

(56) References Cited

U.S. PATENT DOCUMENTS

| 5,057,302 | A |  | 10/1991 | Johnson et al. |
| 5,145,684 | A |  | 9/1992 | Liversidge et al. |
| 5,326,856 | A |  | 7/1994 | Coughlin et al. |
| 5,480,970 | A |  | 1/1996 | Pollak et al. |
| 6,004,531 | A |  | 12/1999 | Archer et al. |
| 6,045,829 | A |  | 4/2000 | Liversidge et al. |
| 6,403,777 | B1 |  | 6/2002 | Cowan |
| 2008/0299227 | A1 | * | 12/2008 | Santamarina .................. 424/692 |

FOREIGN PATENT DOCUMENTS

| WO | WO 99/15195 |   | 4/1999 |
| WO | WO 02090558 | * | 11/2002 |

OTHER PUBLICATIONS

Fineberg et al ('Inhibition of nuclear import mediated by the Rev-arginine rich motif by RNA molecules' Biochemistry v42 (2003) pp. 2625-2633).*
Robertson-Anderson et al ('Single-Molecule studies reveal that DEAD boc protein DDX1 promotes oligomerization of HIV-1 Rev on the Rev response element' Journal of Molecular Biology 410(2011) pp. 959-971).*
Stockman et al., ('SARS:systematic review of treatment effects' PLOS Medicine v3 issue 9 Sep. 2006 pp. 1525-1531).*
Fujii et al. ('Current concepts in SARS treatment' J Infect Chemother 2004 10:1-7).*
Holmes ('SARS cornovirus: a new challenge for prevention and therapy' Journal of Clinical Investigation 2003 11:1605-1609).*
Proximate definition retrieved from http://www.merriam-webster.com/medical/proximate on Sep. 12, 2012 2 pages.*
International Search Report and Written Opinion from PCT/US05/19288, mailed Nov. 18, 2005.
Dessolin et al., "New Bicyclam-AZT Conjugates: design, synthesis, Anti-HIV evaluation, and their interaction with CXCR-4 Coreceptor", J. Med. Chem, 42, pp. 229-241, 1999.
Futaki, et al., "Arginine carrier peptide bearing Ni(II) chelator to promote cellular uptake of histidine-tagged proteins", Bioconjugate chem, 15, pp. 475-481, 2004.
Gokhale, NH, et al., "Inactivation of human angiotensin converting enzyme by copper peptide complexes containing ATCUN motifs", Chem. Commun, 2005, 5916-5918.
Gokhale, et al., "Metallopeptide-promoted inactivation of angiotensin-converting enzyme and endothelin-coverting enzyme 1: toward dual-action therapeutics", J Biol Inorg Chem, 11: 937-947, 2006.
Hohsaka, et al."Incorporation of non-natural amino acids into proteins", Current Opinion in Chemical Biology, 6: 809-815, 2002.
Jin, Y, et al., "Targeted cleavage of HIV Rev. responsivel element RNA by copper ATUCN-Rev derivative peptide complexes", J Am Chem Soc, 128, 410-411, 2006.
Jin, Y., et al., "DNA Cleavage by Copper-ATCUN Complexes. Factors Influencing cleavage mechanism and linearization of dsDNA", J Am Chem Soc, 2005, 127, 8408-8415.
Kratz, et al., "In vitro and in vivo efficacy of acid-sensitive transferrin and albumin doxorubicin conjugates in a human xenograft panel and in the MDA-MB-435 mamma carcinoma model", J of Drug Targeting, vol. 8, No. 5, p. 305-218, 2000.
Li, et al., "Amino acids 1-20 of the hepatitis C virus (HCV) core protein specifically inhibit HCV IRES-dependent translation in HepG2 cells, and inhibit both HCV IRES- and cap-dependent translation in HuH7 and CV-1 cells", J of General Virology, 84, 815-825, 2003.
Long, "Ni(II) Xaa-Xaa-His metallopeptide-DNA/RNA interactions", Accounts of Chemical Research, vol. 32, No. 10, pp. 827-836, Oct. 1999.
Michael, "Metal binding and folding properties of a minimalist Cys2His2 zinc finger peptide", Proc Natl Acad Sci, USA, vol. 89, pp. 4796-4800, Jun. 1992, Biochemistry.
Peled-Zehavi, et al., "Selection of RRE RNA binding peptides using a kanamycin antitermination assay", RNA, 9: 252-261, 2003.
Pulyakov, et al, "Novel Tat-peptide chelates for direct transduction of technetium-99m and rhenium into human cells for imaging and radiotherapy", Bioconjugate Chem, 11: pp. 762-771, 2000.
Roisin, et al., "Inhibition of HIV-1 replication by cell-penetrating peptides binding Rev", J of Biol Chemistry, vol. 279, No. 10, pp. 9208-9214, 2004.
Suzuki, et al., "Possible existence of common internalization mechanisms among arginine-rich peptides", J Biol. Chemistry, vol. 277, No. 4, pp. 2437-2443, Jan. 25, 2002.

* cited by examiner

*Primary Examiner* — Cecilia J Tsang
*Assistant Examiner* — Ronald Niebauer
(74) *Attorney, Agent, or Firm* — Calfee, Halter & Griswold LLP

(57) ABSTRACT

Ligands having a metal binding domain and a targeting domain are provided. The ligands can be used to target, inhibit, and catalytically degrade or inactivate a desired target. Methods of treating a disease or condition using the ligands are also provided.

8 Claims, 29 Drawing Sheets

(a)

| | |
|---|---|
| Angiotensin I (1-10) | Asp-Arg-Val-Tyr-Ile-His-Pro-Phe-His-Leu |
| Angiotensin II (1-8) | Asp-Arg-Val-Tyr-Ile-His-Pro-Phe |
| Bradykinin | Arg-Pro-Pro-Gly-Phe-Ser-Pro-Phe-Arg |
| Bradykinin Inactive Peptide | Arg-Pro-Pro-Gly-Phe-Ser-Pro |

(b)

Gly-Gly-His (GGH)   Lys-Gly-His-Lys (KGHK)   Tyr-Ile-His-Pro-Phe (YIHPF)

(c)

Dose Dependence GGH

Dose Dependence KGHK

Dose Dependence YIHPF

For Cu(GGH)⁻

For Cu(KGHK)⁺

For Cu(YIHPF)⁺

5' FL-labeled    N terminus of Rev linked with ATCUN (A)

(B)

(A)

(B)

Sequence of different Rev peptide derivatives:

Rev1: GGHRev (no linker)
Rev2: GGHGRev
Rev3: GGHGGRev
Rev4: GGHGGGGRev
Rev5: GGHGGGGGGRev
Rev control: binding motif Rev alone Rev peptide: HIV Rev protein (34-50)
Sequence: TRQARRNRRRRWRERQR
Characters: (1) specifically binding HIV RRE RNA
  (2) cellular and nuclear membrane penetrating capacity

Fig. 34

Characterization of Cu – Rev peptide complex $$\varepsilon_{525nm} \sim 100 \text{ cm}^{-1} \text{ M}^{-1}$$

Fluorescence of GFP-RRE protein $\lambda_{em}$ = 395nm, $\lambda_{ex}$ ~ 509nm

In vivo test of GFP cells peptides and Cu-peptide complexes

☐ plasmid with GFP and RRE insert  ■ background cleavage control, plasmid only has GFP (without RRE insert) test of cytotoxicity Captopril IC$_{50}$ = 2.13 nM Captopril-Cyclam IC$_{50}$ = 22.74 nM IC$_{50}$ for [Co(II)capclam]$^{2+}$ = 44.28 nM (A)

(B)

SEQUENCE LISTING

```
<160> NUMBER OF SEQ ID NOS: 43

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 1

Lys Gly His Lys
1
```

```
<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Pro Pro Gly Phe Ser Ala Phe Lys
1               5

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 3

Cys Gly His Lys
1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 4

Val Ile His Asn
1

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 5

Tyr Ile His Pro Phe
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 6

Pro His Gly Gly Gly Trp Gly Gln
1               5

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide motif
```

```
<400> SEQUENCE: 7

His Gly Gly Gly
1

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 8

His Gly Gly Gly Gly
1               5

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 9

His Gly Gly Cys
1

<210> SEQ ID NO 10
<211> LENGTH: 26
<212> TYPE: PRT
<213> ORGANISM: Artificial Sequence
<220> FEATURE:
<223> OTHER INFORMATION: Description of Artificial Sequence: Synthetic
      zinc finger peptide

<400> SEQUENCE: 10

Lys Tyr Ala Cys Ala Ala Cys Ala Ala Ala Phe Ala Ala Lys Ala Ala
1               5                   10                  15

Leu Ala Ala His Ala Ala Ala His Ala Lys
            20                  25

<210> SEQ ID NO 11
<211> LENGTH: 13
<212> TYPE: PRT
<213> ORGANISM: Human immunodeficiency virus

<400> SEQUENCE: 11

Gly Arg Lys Lys Arg Arg Gln Arg Arg Arg Pro Pro Gln
1               5                   10

<210> SEQ ID NO 12
<211> LENGTH: 17
<212> TYPE: PRT
<213> ORGANISM: Human immunodeficiency virus

<400> SEQUENCE: 12

Thr Arg Gln Ala Arg Arg Asn Arg Arg Arg Trp Arg Glu Arg Gln
1               5                   10                  15

Arg

<210> SEQ ID NO 13
<211> LENGTH: 20
<212> TYPE: PRT
<213> ORGANISM: Hepatitis C virus
```

-continued

```
<400> SEQUENCE: 13

Met Ser Thr Asn Pro Lys Pro Gln Arg Lys Thr Lys Arg Asn Thr Asn
1               5                   10                  15

Arg Arg Pro Gln
            20

<210> SEQ ID NO 14
<211> LENGTH: 14
<212> TYPE: PRT
<213> ORGANISM: Unknown
<220> FEATURE:
<223> OTHER INFORMATION: Description of Unknown: Angiotensinogen
      peptide

<400> SEQUENCE: 14

Asp Arg Val Tyr Ile His Pro Phe His Leu Val Ile His Asn
1               5                   10

<210> SEQ ID NO 15
<211> LENGTH: 10
<212> TYPE: PRT
<213> ORGANISM: Unknown
<220> FEATURE:
<223> OTHER INFORMATION: Description of Unknown: Angiotensin I
      peptide

<400> SEQUENCE: 15

Asp Arg Val Tyr Ile His Pro Phe His Leu
1               5                   10

<210> SEQ ID NO 16
<211> LENGTH: 9
<212> TYPE: PRT
<213> ORGANISM: Unknown
<220> FEATURE:
<223> OTHER INFORMATION: Description of Unknown: Bradykinin
      peptide

<400> SEQUENCE: 16

Arg Pro Pro Gly Phe Ser Pro Phe Arg
1               5

<210> SEQ ID NO 17
<211> LENGTH: 4
<212> TYPE: PRT
<213> ORGANISM: Unknown
<220> FEATURE:
<223> OTHER INFORMATION: Description of Unknown: Hemoregulatory
      peptide

<400> SEQUENCE: 17

Ser Asp Lys Pro
1

<210> SEQ ID NO 18
<211> LENGTH: 8
<212> TYPE: PRT
<213> ORGANISM: Unknown
<220> FEATURE:
<223> OTHER INFORMATION: Description of Unknown: Angiotensin II
      peptide

<400> SEQUENCE: 18

Asp Arg Val Tyr Ile His Pro Phe
1               5

<210> SEQ ID NO 19
```

-continued

<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tatgggcaag ggcgaccgca ggacccggcg cggcaagatt tggcgcg        47

<210> SEQ ID NO 20
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gcacctacgg caagtaccgg ccccggaaga agaagtagg        39

<210> SEQ ID NO 21
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gtgccgcgcc aaatcttgcc gcgccgggtc ctgcggtcgc ccttgccca        49

<210> SEQ ID NO 22
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
aattcctact tcttcttccg gggccggtac ttgccgtag        39

<210> SEQ ID NO 23
<211> LENGTH: 27
<212> TYPE: PRT
<213> ORGANISM: Unknown
<220> FEATURE:
<223> OTHER INFORMATION: Description of Unknown: Thx amino acid
      sequence

<400> SEQUENCE: 23

Met Gly Lys Gly Asp Arg Arg Thr Arg Arg Gly Lys Ile Trp Arg Gly
1               5                   10                  15

Thr Tyr Gly Lys Tyr Arg Pro Arg Lys Lys Lys
            20                  25

<210> SEQ ID NO 24
<211> LENGTH: 36
<212> TYPE: PRT
<213> ORGANISM: Thermus thermophilus

<400> SEQUENCE: 24

Gly Gly His Gly Gly Asp Thr Gly Ser Thr Glu Val Gln Val Ala Leu
1               5                   10                  15

Leu Thr Leu Arg Ile Asn Arg Leu Ser Glu His Leu Lys Val His Lys
            20                  25                  30

```
<210> SEQ ID NO 25
<211> LENGTH: 57
<212> TYPE: RNA
<213> ORGANISM: Escherichia coli

<400> SEQUENCE: 25
gggcggccuu cgggcuagac gguggggagag gcuucggcug guccacccgu gacgcuc        57

<210> SEQ ID NO 26
<211> LENGTH: 18
<212> TYPE: PRT
<213> ORGANISM: Staphylococcus aureus

<400> SEQUENCE: 26

Thr Asp Pro Ile Ala Asp Met Leu Thr Arg Val Arg Asn Ala Asn Met
1               5                   10                  15

Val Arg

<210> SEQ ID NO 27
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Arg Gly Ser Arg Pro Ser Gly Ala Glu Arg Arg Arg Arg Ala
1               5                   10                  15

Ala Ala Ala

<210> SEQ ID NO 28
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Gly His Arg Arg Gly Ser Arg Pro Ser Gly Ala Glu Arg Arg
1               5                   10                  15

Arg Ala Ala Ala Ala
            20

<210> SEQ ID NO 29
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Gly His Thr Arg Gln Ala Arg Arg Asn Arg Arg Arg Trp Arg
1               5                   10                  15

Glu Arg Gln Arg
            20

<210> SEQ ID NO 30
<211> LENGTH: 21
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Gly His Gly Thr Arg Gln Ala Arg Arg Asn Arg Arg Arg Arg Trp
1               5                   10                  15

Arg Glu Arg Gln Arg
            20

<210> SEQ ID NO 31
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Gly His Gly Gly Thr Arg Gln Ala Arg Arg Asn Arg Arg Arg Arg
1               5                   10                  15

Trp Arg Glu Arg Gln Arg
            20

<210> SEQ ID NO 32
<211> LENGTH: 16
<212> TYPE: PRT
<213> ORGANISM: Unknown
<220> FEATURE:
<223> OTHER INFORMATION: Description of Unknown: Penetratin
      peptide

<400> SEQUENCE: 32

Arg Gln Ile Lys Ile Trp Phe Gln Asn Arg Arg Met Lys Trp Lys Lys
1               5                   10                  15

<210> SEQ ID NO 33
<211> LENGTH: 38
<212> TYPE: RNA
<213> ORGANISM: Hepatitis C virus

<400> SEQUENCE: 33
cacgcagaaa gcgucuagcc auggcguuag uaugagug                           38

<210> SEQ ID NO 34
<211> LENGTH: 43
<212> TYPE: DNA
<213> ORGANISM: Human immunodeficiency virus

<400> SEQUENCE: 34
aattcggtct gggcgcagcg caagctgacg gtacaggccg ggc                     43

<210> SEQ ID NO 35
<211> LENGTH: 43
<212> TYPE: DNA
<213> ORGANISM: Human immunodeficiency virus

<400> SEQUENCE: 35
ggccgcccgg cctgtaccgt cagcttgcgc tgcgcccaga ccg                     43

<210> SEQ ID NO 36
<211> LENGTH: 32
<212> TYPE: PRT
<213> ORGANISM: Thermus thermophilus
```

<400> SEQUENCE: 36

Gly Asp Thr Gly Ser Thr Glu Val Gln Val Ala Leu Leu Thr Leu Arg
1               5                   10                  15

Ile Asn Arg Leu Ser Glu His Leu Lys Val His Lys Lys Asp His His
            20                  25                  30

<210> SEQ ID NO 37
<211> LENGTH: 30
<212> TYPE: PRT
<213> ORGANISM: Thermus thermophilus

<400> SEQUENCE: 37

Gly Gly His Met Gly Lys Gly Asp Arg Arg Thr Arg Arg Gly Lys Ile
1               5                   10                  15

Trp Arg Gly Thr Tyr Gly Lys Tyr Arg Pro Arg Lys Lys Lys
            20                  25                  30

<210> SEQ ID NO 38
<211> LENGTH: 7
<212> TYPE: PRT
<213> ORGANISM: Unknown
<220> FEATURE:
<223> OTHER INFORMATION: Description of Unknown: Bradykinin
      inactive peptide

<400> SEQUENCE: 38

Arg Pro Pro Gly Phe Ser Pro
1               5

<210> SEQ ID NO 39
<211> LENGTH: 34
<212> TYPE: RNA
<213> ORGANISM: Human immunodeficiency virus

<400> SEQUENCE: 39
ggucugggcg cagcgcaagc ugacgguaca ggcc                              34

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Gly His Gly
1

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Gly His Gly Gly
1               5

<210> SEQ ID NO 42
<211> LENGTH: 7
<212> TYPE: PRT
<213> ORGANISM: Artificial Sequence

```
-continued

<220> FEATURE:
<223> OTHER INFORMATION: Description of Artificial Sequence: Synthetic
      peptide

<400> SEQUENCE: 42

Gly Gly His Gly Gly Gly Gly
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Gly His Gly Gly Gly Gly Gly Gly
1               5
```

US 8,445,431 B2

LIGANDS HAVING METAL BINDING ABILITY AND TARGETING PROPERTIES

CROSS-REFERENCE TO RELATED APPLICATIONS

This application is a National Stage Application of PCT/US2005/19288, filed Jun. 1, 2005, which claims the benefit of U.S. Provisional Application No. 60/575,932, filed Jun. 1, 2004.

BACKGROUND OF THE INVENTION

The present invention relates to ligands having metal binding ability and targeting properties. The present invention further relates to ligands having a metal species and to the use of such ligands to target, and either catalytically degrade or inactivate a desired target entity through the use of a metal catalyst. The present invention additionally relates to ligands that may recognize a desired target entity.

Traditional drug design often focuses on compounds that inhibit a desired target in order to keep the target from functioning. These compounds may provide drugs that effectively treat certain diseases. However, these traditional drug designs may not be completely effective in treating certain diseases or conditions because some targets, such as viruses, can mutate and the drug compound may become ineffective. Additionally, the compounds may produce undesirable side effects because of the dosages required for the compounds to effectively treat or control the disease or condition.

Thus, there remains a need in the art for drug compounds that may inhibit and degrade or inactivate a target in order to prevent the target from causing the disease or condition for which the drug is administered.

BRIEF DESCRIPTION OF THE SEVERAL VIEWS OF THE DRAWINGS

The following detailed description of the embodiments of the present invention can be best understood when read in conjunction with the following drawings, in which.

control reaction, only [RRE]=10 µM and ascorbate; R: cleavage reaction, where [RRE]=10 µM, [copper-Rev1 complex]/[RRE]=1:1 with excess ascorbate in 20 mM HEPES with 100 mM NaCl at 37° C. for 6 hr. (b) a schematic illustration of the stem loop structure adopted RRE RNA IIB, showing the cleavage sites (SEQ ID NO: 39).

Figure 24:
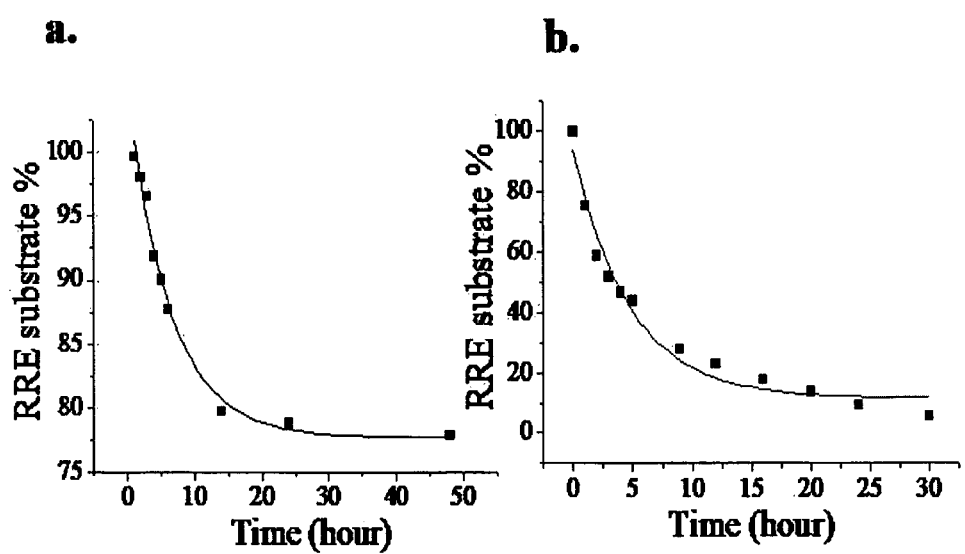

FIG. 24. The cleavage reaction, [RRE]=5 µM, [copper-Rev1 complex]/[RRE]=1:1 in 20 mM HEPES with 100 mM NaCl at 37° C., was followed with time by monitoring the decrease of RRE RNA substrate. (a) the reactions were carried out under the hydrolytic condition, t1=6.36 h, $R^2$=0.99 (b) the reactions were carried out under the oxidative condition with ascorbate as co-reactant, t1=4.75 h, $R^2$=0.98.

Figure 25:
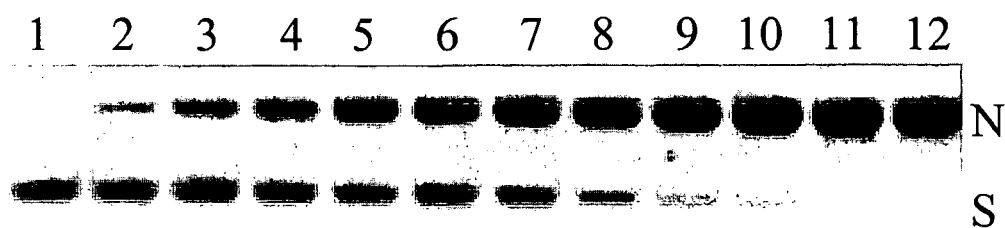
Figure 25:
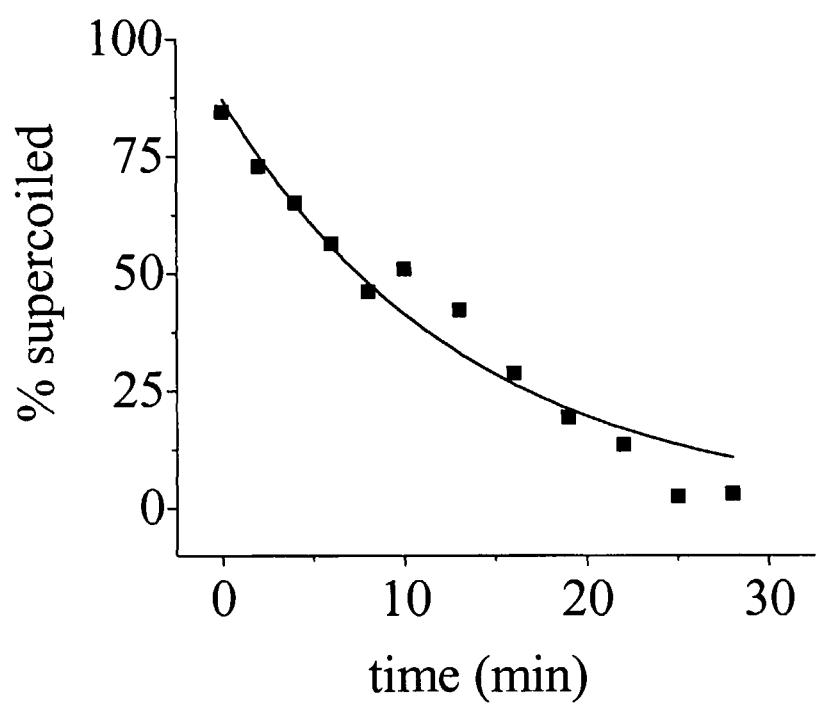

FIG. 25 illustrates cleavage activity of [GGH-Cu]$^-$ monitored by 0.8% agarose gel electrophoresis, where [DNA]=50 µM, [[GGH-Cu]$^-$]=25 µM, [ascorbate]=250 µM. Time course measured in 10 mM Tris buffer, pH=7.4, 37° C., showing the disappearance of supercoiled DNA (S), (1) 0 min, (2) 2 min, (3) 4 min, (4) 6 min, (5) 8 min, (6) 10 min, (7) 13 min, (8) 16 min, (9) 19 min, (10) 22 min, (11) 25 min, (12) 28 min. (A) Gel image showing nicked (N) and supercoiled (S) DNA. (B) Reaction curve, showing a pseudo-first order kinetic profile ($R^2$=0.952), $k_{obs}$~0.07 min$^{-1}$.

Figure 26:
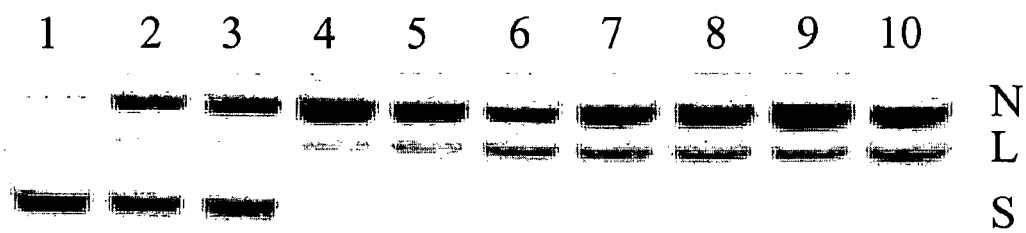
Figure 26:
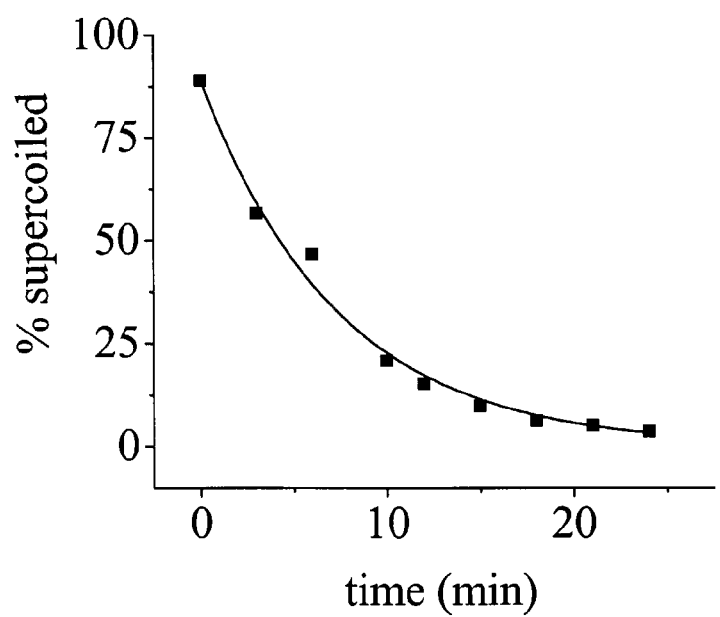

FIG. 26 illustrates cleavage activity of [KGHK-Cu]$^+$ (SEQ ID NO: 1) monitored by 0.8% agarose gel electrophoresis, where [DNA]=50 µM, [[KGHK-Cu]$^+$]=25 µM (SEQ ID NO: 1), [ascorbate]=250 µM. Time course measured in 10 mM Tris buffer, pH=7.4, 37° C., showing the disappearance of supercoiled DNA (S), (1) 0 min, (2) 3 min, (3) 6 min, (4) 9 min, (5) 12 min, (6) 15 min, (7) 18 min, (8) 21 min, (9) 24 min, (10) 27 min (DNA began to smear). (A) Gel image showing nicked (N), linear (L), and supercoiled (S) DNA. (B) Reaction curve, showing a pseudo-first order kinetic profile ($R^2$=0.99), $k_{obs}$~0.14 min$^{-1}$.

Figure 27:
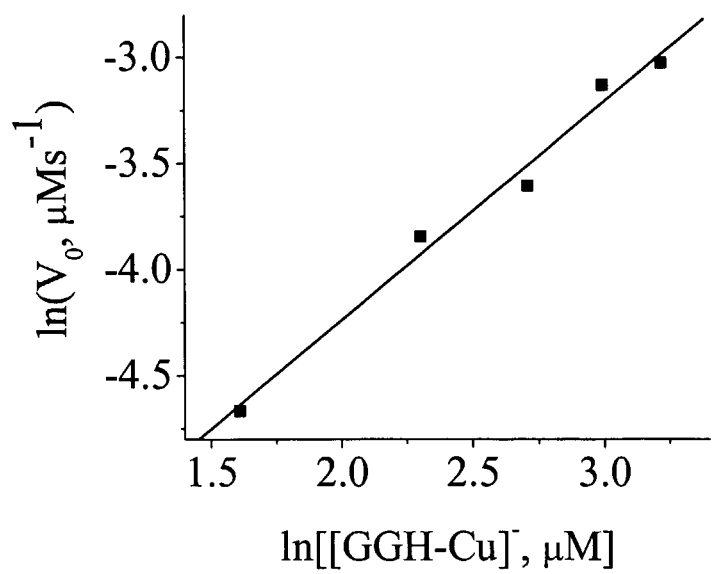
Figure 27:
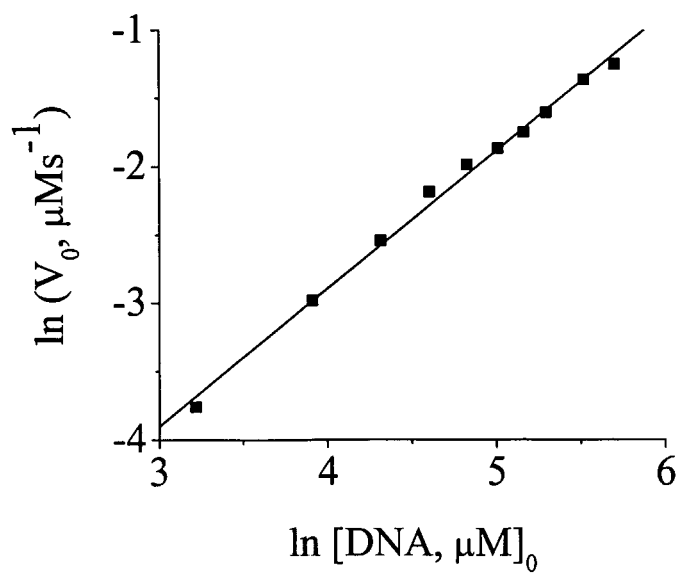

FIG. 27 illustrates (A) The dependence of ln $V_0$ versus ln [[GGH-Cu]$^-$]. Fitting to equation (5), where $k_{obs}$=$k_2$[DNA], yielded $k_2$~39 M$^{-1}$s$^{-1}$ and m~1. (B) The dependence of ln$V_0$ versus ln[DNA]$_0$ was similarly fitted, where $k_{obs}$=$k_2$[complex], yielded $k_2$~39M$^{-1}$s$^{-1}$ and m~1.

Figure 28:
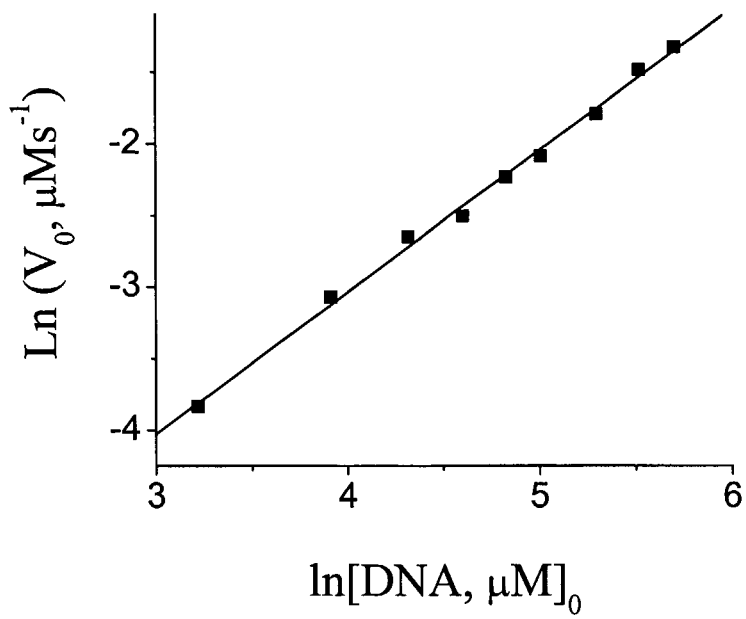

FIG. 28 illustrates the dependence of ln$V_0$ versus ln [DNA]$_0$, where $k_{obs}$=$k_2$[complex], yielded $k_2$~93 M$^{-1}$s$^{-1}$ and m~1.

Figure 29:
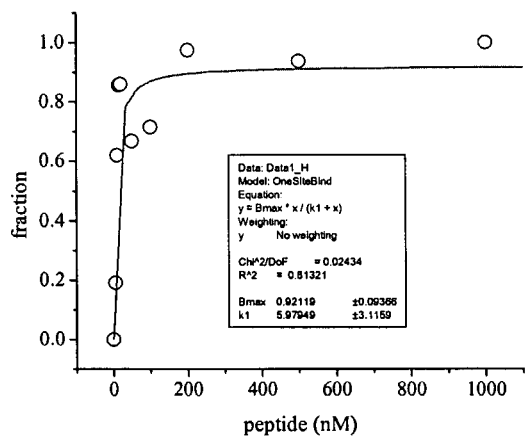

FIG. 29 illustrates Peptide binding to HCV IRES monitored by fluorescence methods.

Figure 30:
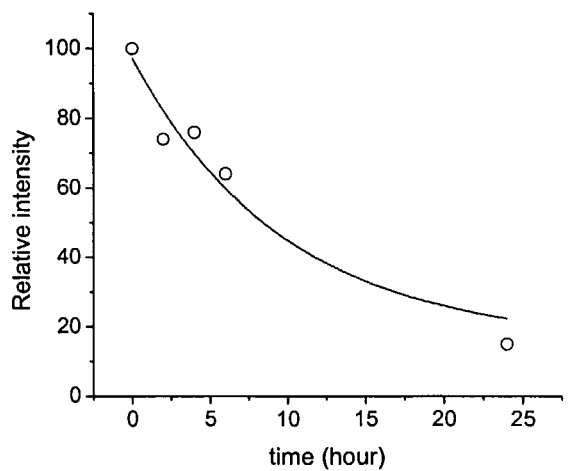

FIG. 30 illustrates a plot of the relative intensity of the reactant RNA versus reaction time for the oxidative cleavage of hepatitis C IRES.

Figure 31:
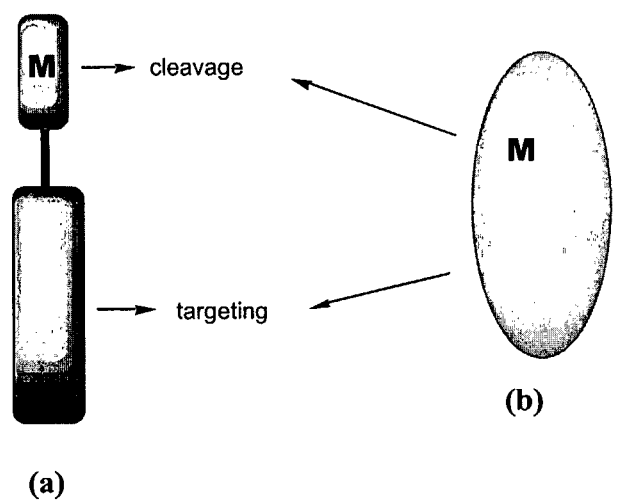

FIG. 31 illustrates a general metal-ligand complexes, in accordance with embodiments of the present invention, that contains discrete metal binding and targeting domains.

Figure 32:
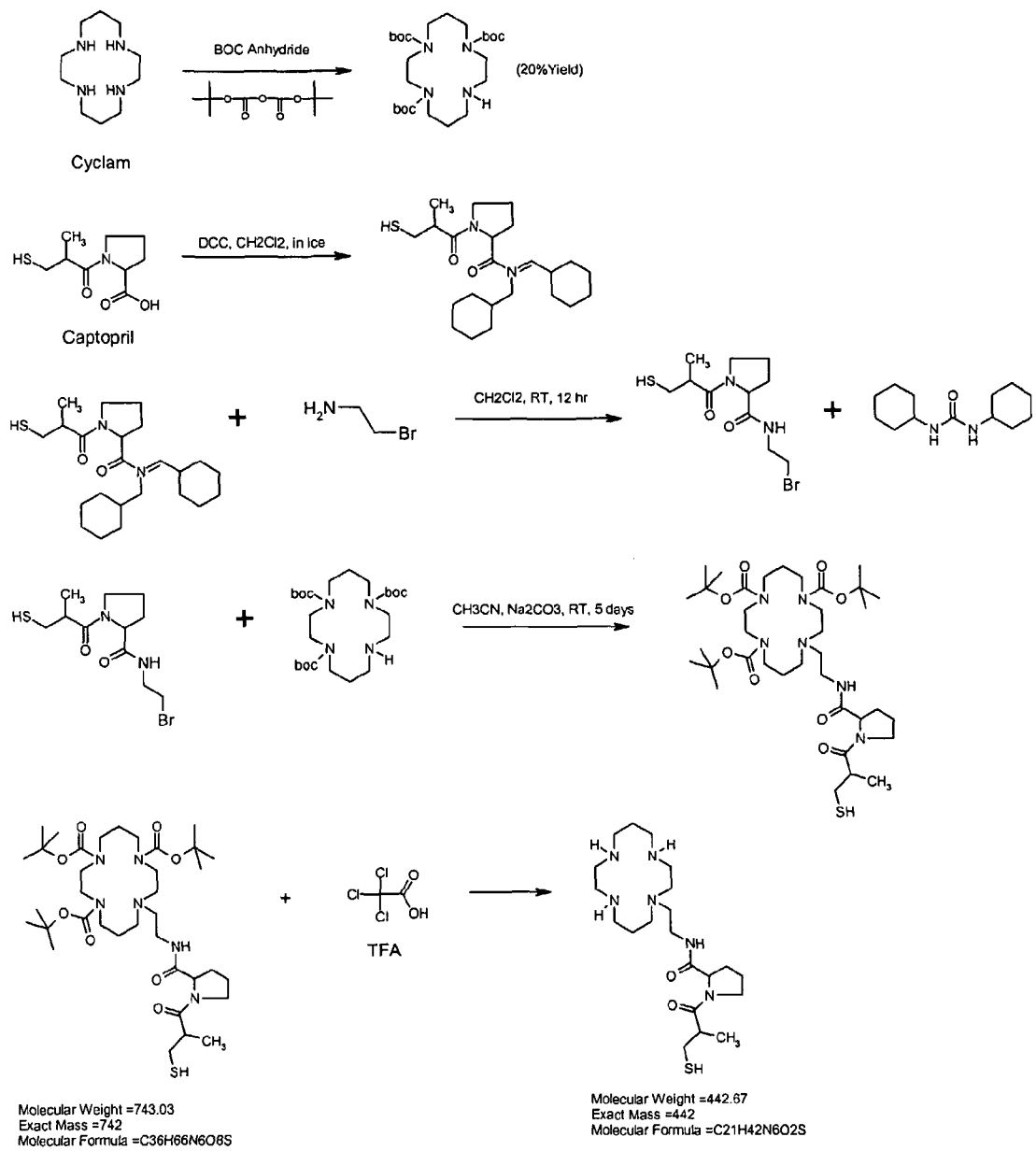

FIG. 32 illustrates the synthesis of a ligand comprising a cyclam-captopril analog.

Figure 33:
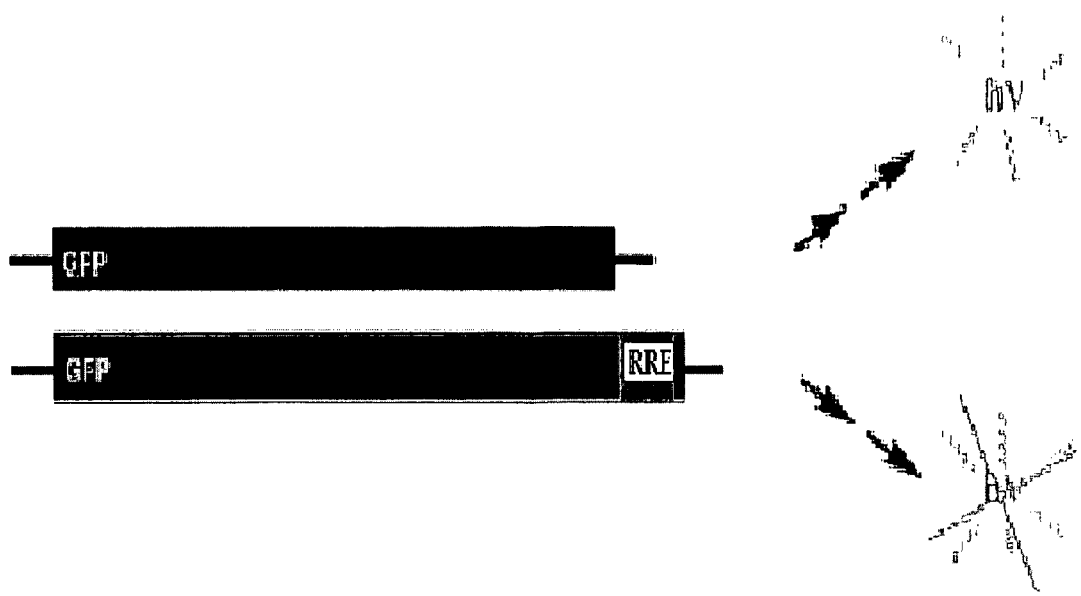

FIG. 33 illustrates the strategy of in vivo cell assays of RRE RNA cleavage chemistry.

FIG. 34 illustrates the sequences used in in vivo cell assays of RRE RNA cleavage chemistry (SEQ ID NOS 40-43 and 12, respectively in order of appearance).

Figure 35:
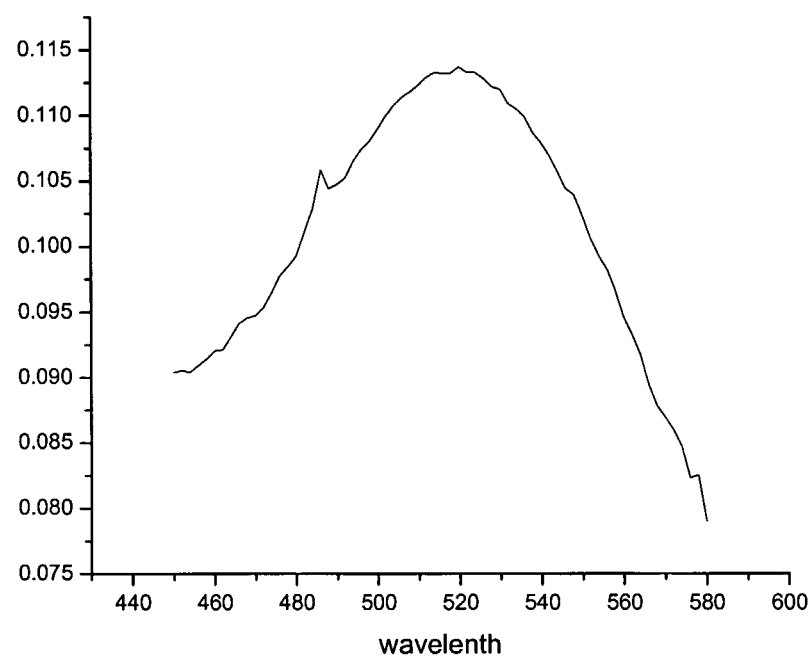

FIG. 35 illustrates the characterization of a Cu-Rev peptide complex.

Figure 36:
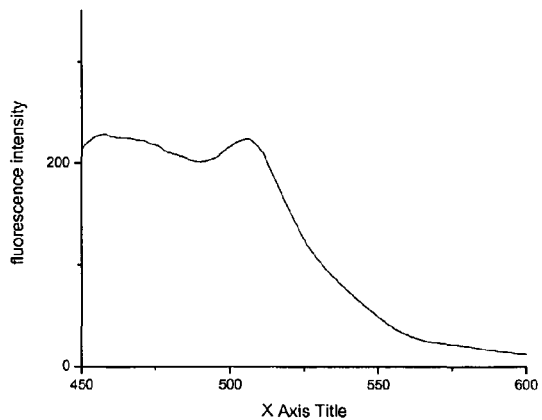

FIG. 36 illustrates fluorescence of an GFP-RRE protein.

Figure 37:
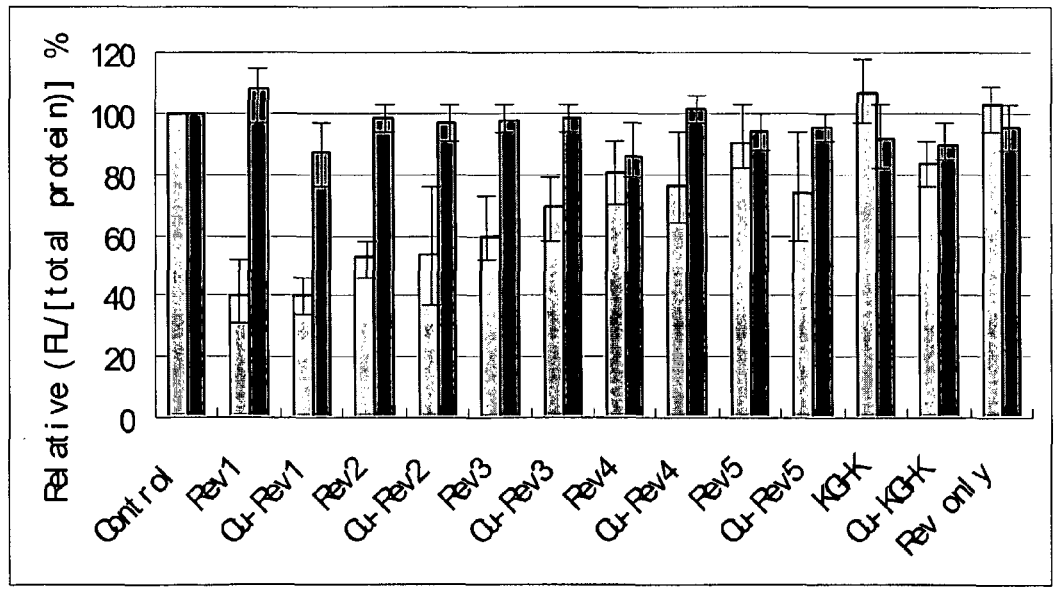

FIG. 37 illustrates in vivo tests of GFP cell peptides and Cu-peptide complexes.

Figure 38:
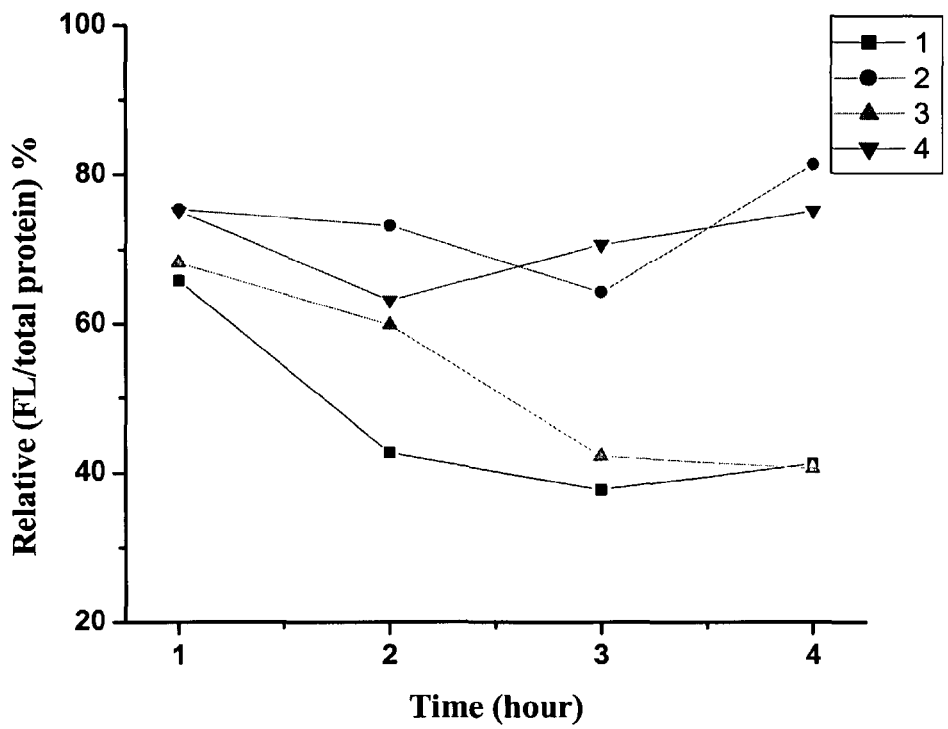

FIG. 38 illustrates the time course of the in vivo test of Rev1 and Rev1-Cu. The effect of Rev1 peptide and Rev1-Cu complex on GFP-RRE system were tested hourly in vivo under different conditions. 1, 3. Rev1 and Rev1-Cu with 1 hour pre-incubation and adding one aliquot every hour, respectively. 2, 4. Rev1 and Rev1-Cu without pre-incubation and with adding only one aliquot at the starting point (hour 0, IPTG is added), respectively. Relative (fluorescence intensity of GFP/total protein) against the control was quantitated for each sample. Each point is the average of triplicate.

Figure 39:
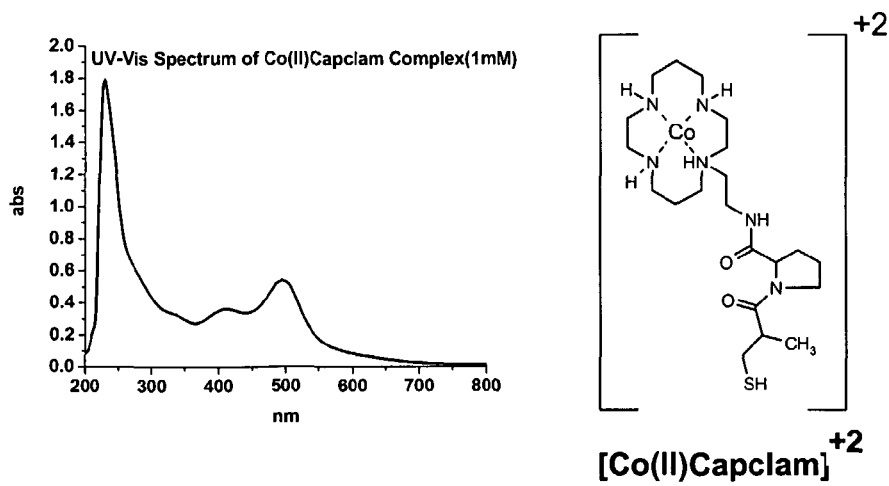

FIG. 39 illustrates the proposed structure for Co(II) Capclam complex.

Figure 40:
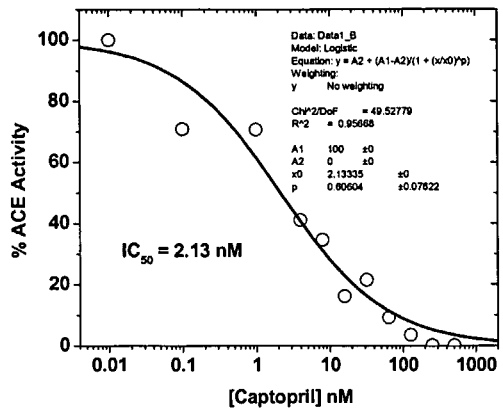
Figure 40:
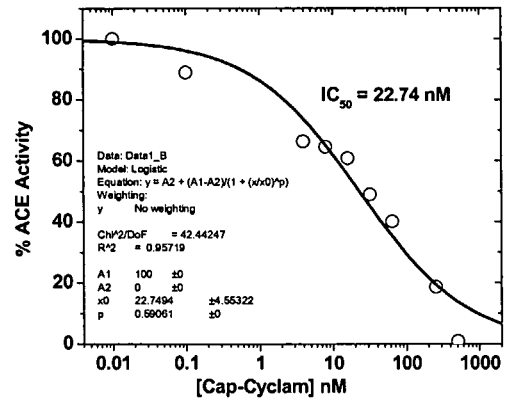
Figure 40:
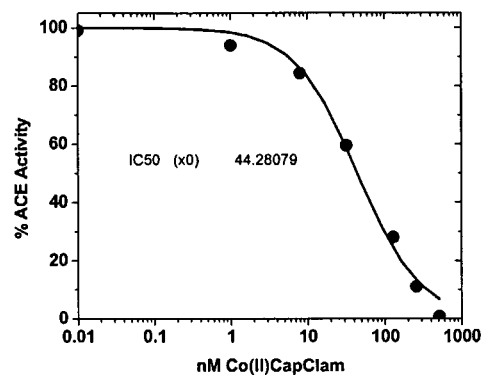

FIG. 40 illustrates comparative IC$_{50}$'s for recombinant human ACE Inhibition by Captopril-Cyclam (Capclam) complexes relative to copper and cobalt peptide complexes, and Demonstration of Inactivation by Cobalt Capclam.

Figure 41:
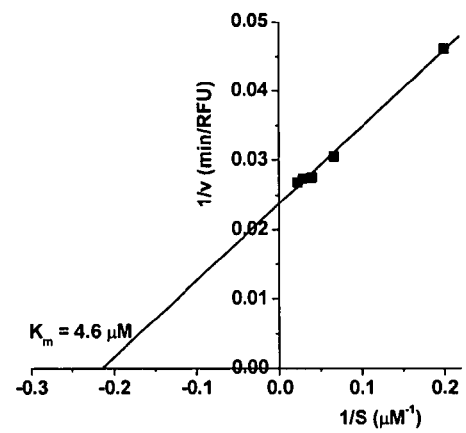

FIG. 41 illustrates the determination of $K_m$ value for the Mca-Arg-Pro-Pro-Gly-Phe-Ser-Ala-Phe-Lys(Dnp)-OH (SEQ ID NO: 2) substrate with 5 nM TLN enzyme. Figure showing the determination of $K_m$ value for the Mca-Arg-Pro-Pro-Gly-Phe-Ser-Ala-Phe-Lys(Dnp)-OH (SEQ ID NO: 2) substrate with 5 nM TLN enzyme.

Figure 42:
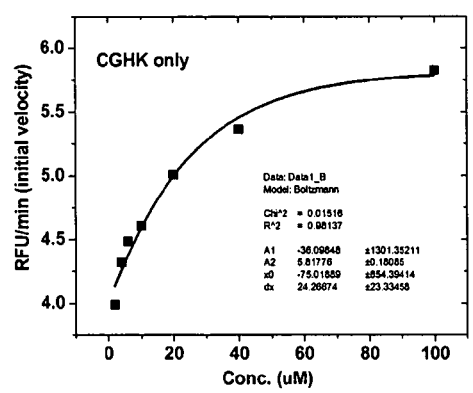
Figure 42:
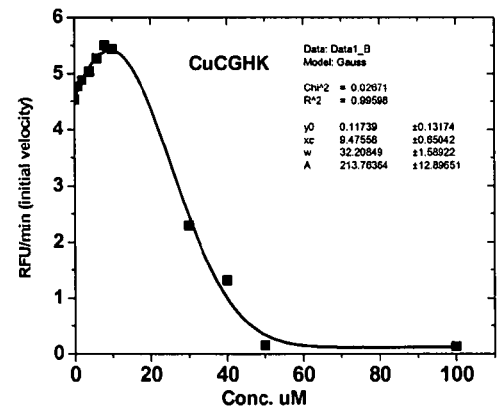

FIG. 42 illustrates the data fit for the dose dependent (A) activation by CGHK peptide (SEQ ID NO: 3) (B) inhibition by Cu(CGHK) (SEQ ID NO: 3).

Figure 43:
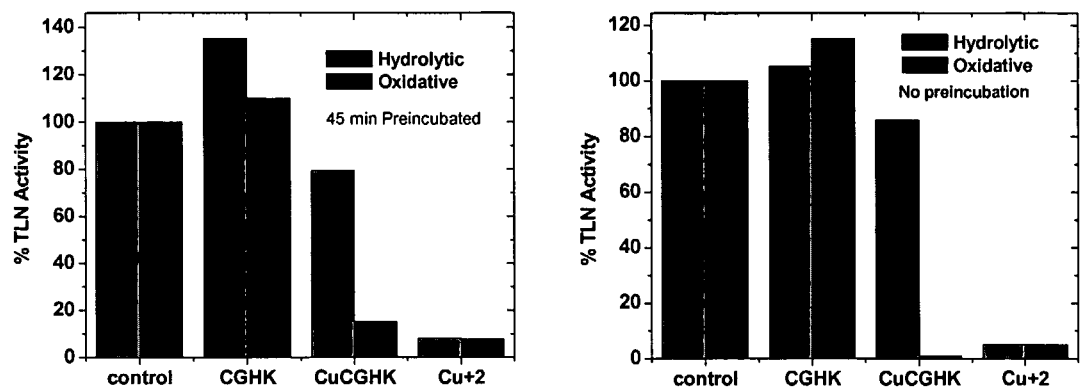

FIG. 43 illustrates the effect of preincubation (45 min) on the inhibitory potency of the CuCGHK (20 uM) (SEQ ID NO: 3) complex under oxidative (with 0.5 mM ASC ascorbate) and hydrolytic (no ascorbate) conditions.

Figure 44:
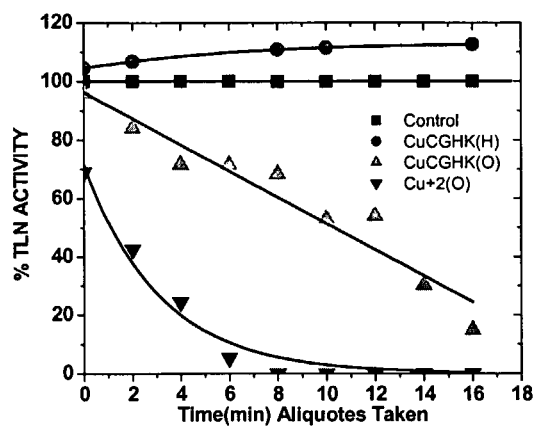

FIG. 44 illustrates time dependent inactivation of TLN enzyme by 1 µM Cu(CGHK) (SEQ ID NO: 3): 0.1 mL aliquots were taken at 2 min interval from a 2 mL reaction mixture [containing TLN (5 nM), ascorbate (0.5 mM), Inhibitor (1 uM) at indicated final concentrations] into wells of 96 well plates containing 1 uL of 1 mM substrate (final conc. 10 uM in 0.1 mL). RFU increase data collected with 4 min time interval. % ACTIVITY is determined by relative RFU/Min (initial velocity).

DETAILED DESCRIPTION OF EMBODIMENTS OF THE INVENTION

The present invention will now be described with occasional reference to the specific embodiments of the invention. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications, patent applications, patents, and other references mentioned herein are incorporated by reference in their entirety.

In accordance with embodiments of the present invention, ligands having at least one metal binding domain and at least one targeting domain are provided. The ligands may also have a metal bound by the metal binding domain to form metal-ligand complexes. For purposes of defining and describing the present invention, the term "metal binding domain" shall be understood as referring to a moiety having at least one motif that is capable of binding at least one metal. For purposes of defining and describing the present invention, the term "targeting domain" shall be understood as referring to at least one peptide, portion of a protein, antibody, or other moiety that may bind to a desired target. It will be understood that the metal binding domain and the targeting domain may comprise a single domain or more than one domain. For example, a single metal binding domain may also target a desired target entity.

Figure 1:
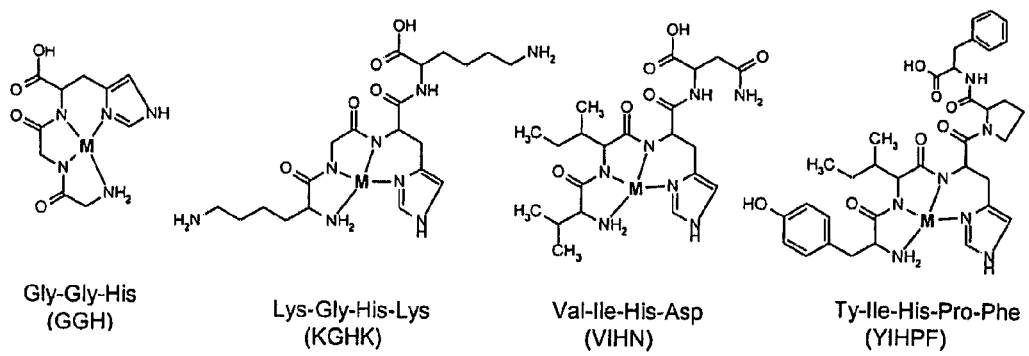
FIG. 1 illustrates metal binding domains in accordance with embodiments of the present invention (SEQ ID NOS 1, 4, and 5, respectively in order of appearance from left to right)

The metal binding domain may comprise any suitable metal binding domain that may be attached to any suitable targeting domain. In one example, the metal binding domain may comprise an amino terminal Cu(II) and Ni(II) binding ("ATCUN") motif. The ATCUN motif comprises a peptide having (1) a free $NH_2$—terminus, (2) two intervening peptide nitrogens, and (3) a histidine (H) residue at position 3. The ATCUN motif peptides are capable of binding metals such as Cu(II), Ni(II), Fe(III), ARM), Co(II), and Co(III). Specific examples of ATCUN motifs include, but are not limited to, GGH, KGHK (SEQ ID NO: 1), VIHN (SEQ ID NO: 4), and YIHPF (SEQ ID NO: 5). FIG. 1 illustrates these specific ATCUN motifs with a metal M bound by the motif.

In another example, the metal binding domain may comprise the ATCUN motif having modifications with non-natural amino acids containing metal-binding groups. The modifications may be non-natural amino acids derived from modifications at the N- and C-termini of the ATCUN motif. For example cyclised lysines and pyridyl/pyrazolyl terminal secondary amino functionalities may be used.

Figure 2:
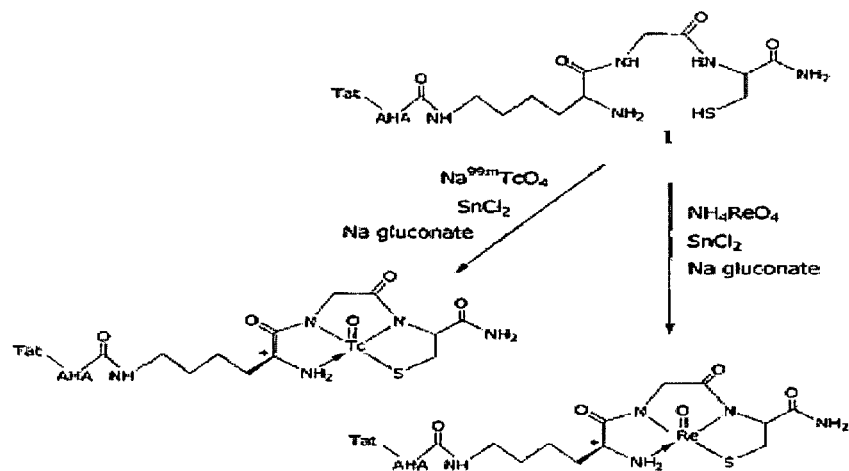
FIG. 2 illustrates a scheme for forming metal binding domains in accordance with embodiments of the present invention.
Figure 3:
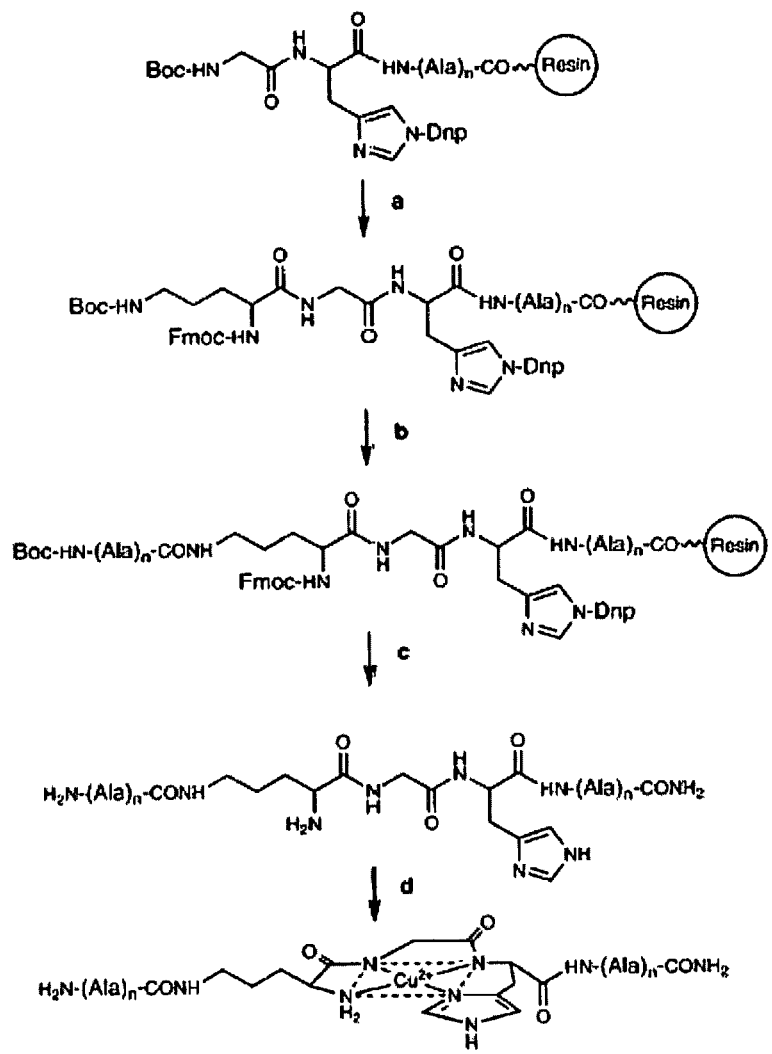
FIG. 3 illustrates another scheme for forming metal binding domains in accordance with embodiments of the present invention.

In another example, the N-terminus of a peptide may have an ATCUN motif thereon. A suitable N-terminus modification is described in *Current Opinion in Chemical Biology* 2002, 6, 809-815. The C-terminus of a peptide may have an ATCUN motif thereon. An example of a scheme for such a metal binding domain is illustrated in FIG. 2. This type of metal binding domain is discussed in *Bioconjugate Chem.* 2000, 11, 762-771. Another suitable metal binding domain is a peptide having an ATCUN motif on an internal portion of the peptide. A scheme for preparing one such domain is illustrated in FIG. 3 and discussed in *Accounts of Chemical Research* 1999, 32(10), 827. It will be understood that the peptide may be any suitable peptide of any suitable length. It will be further understood that the ATCUN motif may be any suitable motif.

In another example, metal binding domains having an ATCUN motif may be modified to enhance metal reactivity. The N-terminus of the ATCUN motif may be modified to replace primary amino functionality with secondary amino function. For example, a Schiff base may be utilized. In addition point variations of one or more of the amino acids in the ATCUN motif may be made (except the His in the third position). For example, Xaa-G-H or G-Xaa-H may be used where Xaa represents any amino acid. In addition substitution of L- for D-configuration amino acids may be made for one or more of the amino acids in the ATCUN motif me. In both cases, such modifications may induce steric and electronic changes in the ATCUN motifs resulting in a modulation of metal reactivity.

In another example, the metal binding domain may comprise an octa-repeat motif from the prion protein having a sequence of PHGGGWGQ (SEQ ID NO: 6). In a further example, the metal binding domain may comprise a motif comprising histidine (H) as the first residue and glycine (G) as the third residue starting from the N-terminus of the motif. For example, the metal binding domain may comprise HGG, HGGG (SEQ ID NO: 7), HGGGG (SEQ ID NO: 8), HGGC (SEQ ID NO: 9), and the like. This domain may be repeated within a peptide sequence and cysteine (C) residues may be incorporated to increase metal binding affinity. It will be understood that the motif may comprise only a portion or portions of the metal binding domain. In another example, the metal binding domain may comprise a motif having histidine (H) as the third residue from the N-terminus. For example, the metal binding domain may comprise Xaa-Xaa-H with Xaa being any amino acid. The motif may be repeated in the metal binding domain, and the motif may comprise only a portion or portions of the metal binding domain. In one example, the metal binding domain may comprise a short peptide of less than about 30 amino acids containing a motif having H as the third residue and or a motif having H as the first residue and G as the third residue or having a motif of Xaa-H-Xaa-Gly-Xaa-anywhere within the sequence.

Figure 4:
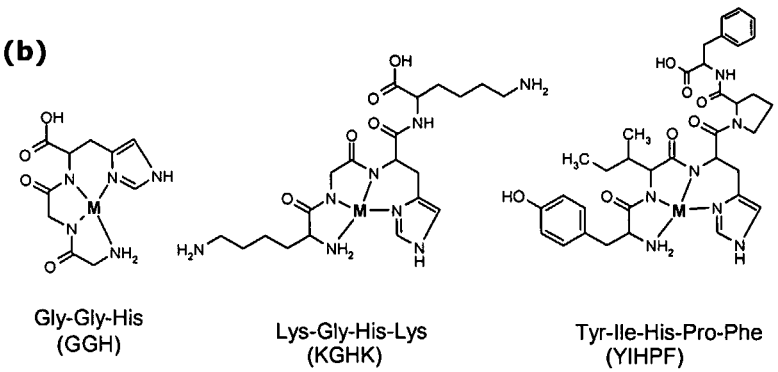
FIG. 4 illustrates (*a*) Peptides involved in the Renin-Angiotensin system (SEQ ID NOS 15, 18, 16, and 38, respectively in order of appearance) (residues in bold are the peptide fragments used in the present study); (*b*) Peptides used in the present study shown in metal complexed forms (M=$Cu^{2+}$), (SEQ ID NOS 1 and 5); and (*c*) Crystallographically defined association of lisinopril (inhibitor) with one of the active sub-sites of ACE (FIG. 4(*c*)). Ligand KGHK (SEQ ID NO: 1) may mimic the lysine-like chain binding to pocket 51'.
Figure 4:
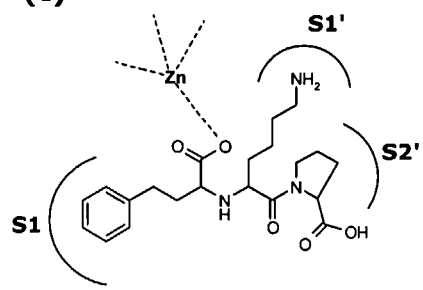
Figure 5:
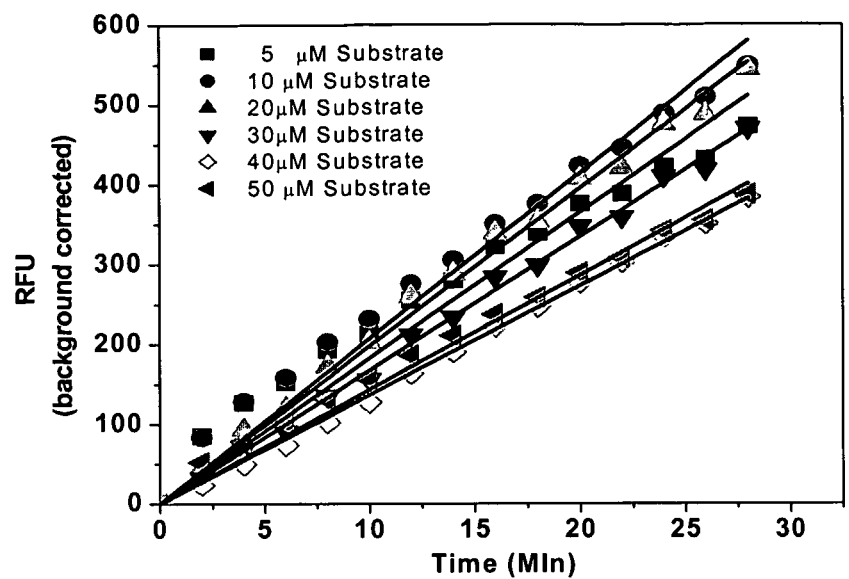
FIGS. 5-8 are plots used for determination of kinetic constants.
Figure 6:
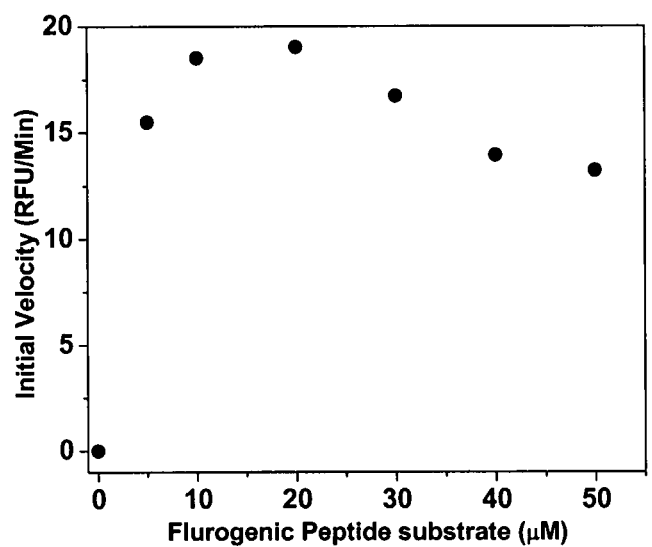
Figure 7:
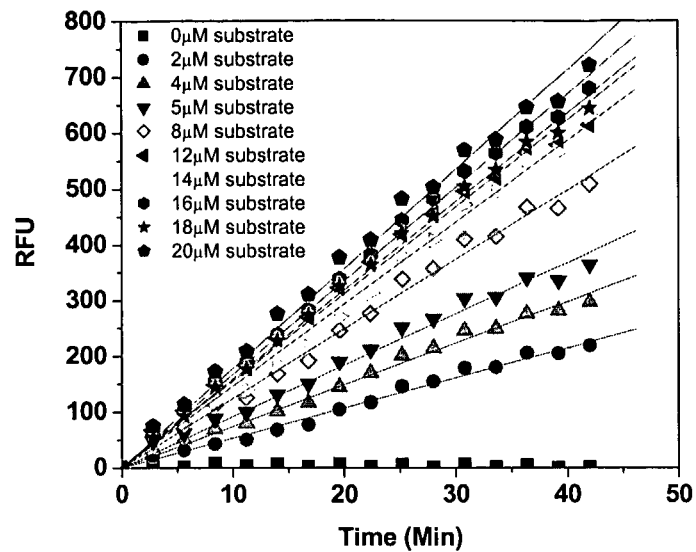
Figure 8:
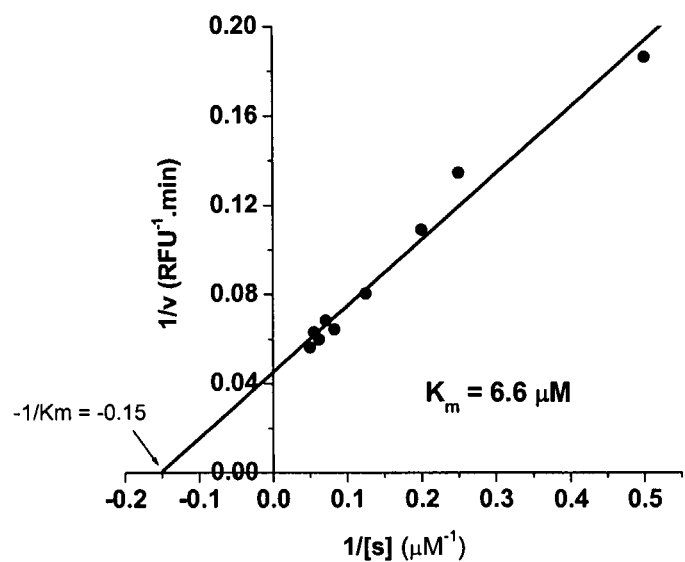
Figure 9:
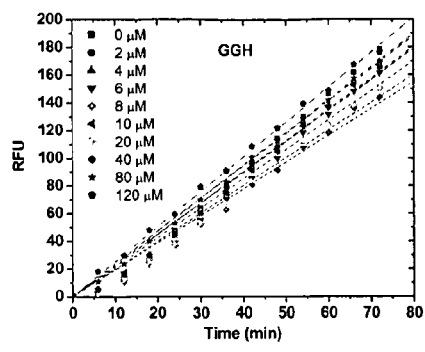
FIGS. 9-12 are plots used for determination of $IC_{50}$ values for rhACE inhititors (KGHK and YIHPF are disclosed as SEQ ID NOS 1 and 5, respectively).
Figure 9:
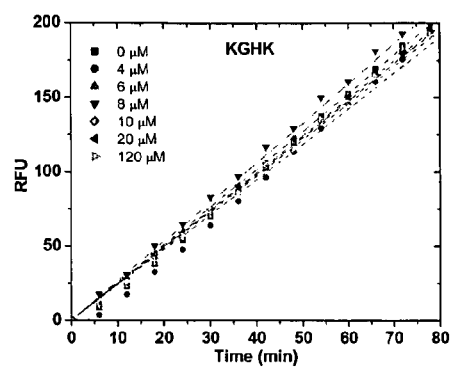
Figure 9:
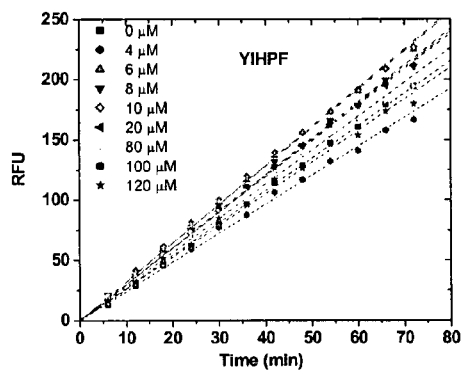
Figure 9:
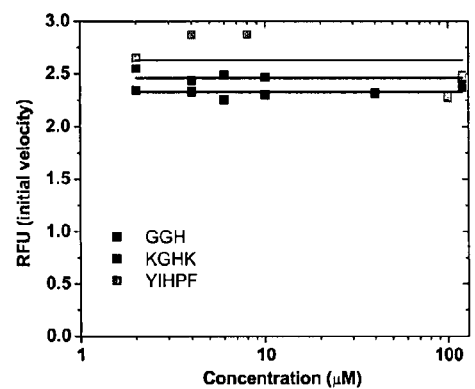
Figure 10:
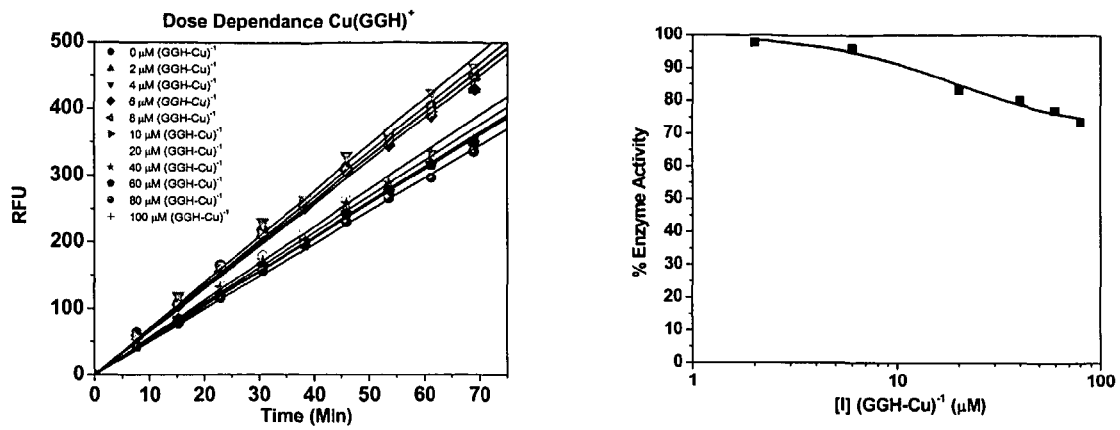

The metal binding domain may comprise zinc finger peptides having a zinc binding unit comprising two cysteine (Cys) and two histidine (His) residues. One such suitable zinc finger peptide is Lys-Tyr-Ala-Cys-Ala-Ala-Cys-Ala-Ala-Ala-Phe-Ala-Ala-Lys-Ala-Ala-Leu-Ala-Ala-His-Ala-Ala-Ala-His-Ala-Lys (SEQ ID NO: 10) which is reported in *Proc Natl Acad Sci USA*. 1992 Jun. 1; 89(11):4796-800. The metal binding domain may comprise short peptide conjugates with small molecular weight synthetic metal binding motifs. The small molecular weight synthetic metal binding motif may be selected to bind a desired metal. For example, the synthetic metal binding motif may comprise cyclam, bipyridyl, terpyridine, porphyrin, and TREN (tris(2-aminoethyl)amine). The metal binding domain may comprise Xaa-Xaa-cyclam/bipyridyl and the like. Additionally, the metal binding domain may comprise a peptide mimic with metal binding abilities. For example, the ACE inhibitors captopril or lisinopril (FIG. 4(c)) are two suitable examples.

In another example the metal binding domain may be a cyclam chelating motif that is tagged to a targeting peptide. In another example the metal binding domain may be a cyclam chelating motif that is tagged to captopril or lisinopril. The synthesis of such a ligand comprising a metal binding domain cyclam with a targeting captopril is illustrated in FIG. 32.

In another embodiment, the metal binding domain may comprise the metalloligands disclosed in U.S. Pat. No. 6,403,777 to Cowan. The metalloligand may be a metal aminoglycoside as disclosed in the Cowan patent. It will be understood that the motifs illustrated above may comprise only a portion or portions of the metal binding domains of the present invention. It will be further understood that only portions of the motifs illustrated above may be utilized as the metal binding domains of present invention. It will also be understood that the motifs above may have one or more amino acid substituted for any other amino acid or amino acid analog.

The metal binding domain is exposed to a desired metal so that the metal is bound to the metal binding domain and metal-ligand complexes may be formed. It will be understood that the metal binding domain may be exposed to the metal either before the formation of the ligand with the targeting domain or after the formation of the ligand. Any suitable metal may be used. Examples of suitable metals include transition metals such as Cu(II), Ni(II), Fe(III), Al(III), Co(II), Co(III), Zn (II), and other second and third row transition metal ions, and non-transition metals such as Al(III). The metal may be bound to the metal binding domain in any suitable manner. For example, a solution of 1 mM peptide in 10 mM Tris buffer (pH=7.4) may be mixed with 0.95 mM $CuCl_2$ in 10 mM Tris buffer solution in a 1:1 ratio. It will be understood that any other suitable method may be used.

The targeting domain may comprise any suitable domain that may be attached to a metal binding domain. The targeting domain may be any suitable peptide, portion of a protein, antibody, or other suitable moiety such as a metalloligand. It will be understood that the targeting domain may be selected in order to target a desired target species. In one example, the targeting domain may comprise a peptide or peptides that bind tightly and specifically to nucleic acids or proteins. Examples of such peptides include Tat having a sequence of GRKKRRQRRRPPQ (SEQ ID NO: 11), which is a peptide derived from the natural HIV Tat protein which binds specifically to a target HIV TAR RNA motif, and Rev having a sequence of TRQARRNRRRRWRERQR (SEQ ID NO: 12), which is a peptide derived from the natural HIV RRE binding protein that binds to a target HIV RRE RNA moiety. Another example of a targeting domain in accordance with the present invention is amino acids 1-20 of the hepatitis C virus (HCV) core protein having a sequence of MSTNPKPQRKTKRNT-NRRPQ (SEQ ID NO: 13). This peptide has been shown to bind to the internal ribosomal entry site (IRES) of HCV as reported in the *Journal of General Virology*. 2003, 84, 815-825. In another example, the targeting domain can comprise Y-(D)-RFK, where (D) indicates a (D) configuration amino acid, which binds to the IRES of HCV.

In another example, the targeting domain may comprise peptides that are substrates for proteases such as Angiotensin converting enzyme (ACE, petidyl dipeptidase A; EC 3.4.15.1) or other peptides involved in the Renin-Angiotensin system such as Angiotensinogen (1-14) Asp-Arg-Val-Tyr-Ile-His-Pro-Phe-His-Leu-Val-Ile-His-Asn (SEQ ID NO: 14), Angiotensin I (1-10): Asp-Arg-Val-Tyr-Ile-His-Pro-Phe-His-Leu (SEQ ID NO: 15); Bradykinin: Arg-Pro-Pro-Gly-Phe-Ser-Pro-Phe-Arg (SEQ ID NO: 16); Hemoregulatory peptide: N-acetyl-Ser-Asp-Lys-Pro (SEQ ID NO: 17); Angiotensin II (1-8): Asp-Arg-Val-Tyr-Ile-His-Pro-Phe (SEQ ID NO: 18); and Bradykinin Inactive Peptide: Arg-Pro-Pro-Gly-Phe-Ser-Pro (SEQ ID NO: 38).

In yet another example, the targeting domain can comprise a ribosomal protein (thx) from the thermophilic organism *Thermus thermophilus*. This targeting domain can be modified to with an N-terminal metal binding domain. This protein adds to the complement of regular bacterial ribosomal proteins and disrupts ribosomal function. This metalloprotein can be used as an anti-infective to mediate catastrophic damage to bacterial ribosomal RNA. The ribosomal protein Thx can be cloned into expression vector pET21 between Nde I and EcoR I cloning sites using the synthetic oligonucleotides as follows: forward 5'-TAT GGG CAA GGG CGA CCG CAG GAC CCG GCG CAA GAT TTG GCG CG-3' (SEQ ID NO: 19) and 5'-GCA CCT ACG GCA AGT ACC GGC CCC GGA AGA AGA AGT AGG-3' (SEQ ID NO: 20), and backward 5'-GTG CCG CGC CAA ATC TTG CCG CGC CGG GTC CTG CGG TCG CCC TTG CCC A-3' (SEQ ID NO: 21) and 5'-AAT TCC TAC TTC TTC TTC CGG GGC CGG TAC TTG CCG TAG-3' (SEQ ID NO: 22). The amino acid sequence of Thx is MGKGDRRTRR GKIWRGTYGK YRPRKKK (SEQ ID NO: 23) with calculated pI being 11.9. A metal binding sequence GGH can also be included at the N-terminus.

In another example, the targeting domain can comprise an amino acid sequence that is based on residues 19-50 of the S15 protein of *Thermus thermophilus*. In one example, the metal binding domain can comprise GGH and a linker sequence $(G)_x$, where x is any suitable number. Thus, in one example, the ligand can comprise GGH-$(G)_x$-GDTG-STEVQVALLTLRINRLSEHLKVHKKDHH (SEQ ID NO: 24). This ligand targets the 57 nt RNA corresponding to nucleotides 584-590/649-667/739-757 of *E. coli* rRNA: 5'-gggcg gccuu cgggc uagac ggugg gagag gcuuc ggcug gucca cccgu gacgc uc-3' (SEQ ID NO: 25). This ligand can inhibit bacterial survival.

In another example, the targeting domain may comprise peptides or portions of proteins responsible for binding. For example, Tat or Rev may be used. Additionally portions of *Staphylococcus aureus*: S8 residues 4-21: TDPIADML-TRVRNANMVR (SEQ ID NO: 26), and residues 30-32, 56-57, 82-92, 107-111, and 122-125 can be used. In another example, the targeting domain may comprise any combinatorially-derived peptides that bind specifically. An example of a suitable combinatorially derived peptide is RSG which has a sequence of RRGSRPSGAERRRRRAAAA (SEQ ID NO: 27) and that targets the HIV RRE RNA moiety. Any other suitable synthetic target peptide may be used. In another example of the present invention, the targeting domain may comprise an antibody. For example, antibodies to cancer cell or other pathogens may be utilized.

The ligands of the present invention may be made in any suitable manner. In addition, the metal binding domains and the targeting domains can be linked in any suitable manner. In one example, the metal binding domains and the targeting domains are covalently bonded. In another example, the metal binding domain is linked to the targeting domain via x linker amino acid residues, where x=0, 1, 2, and so on. One example of a ligand comprises a GGH metal binding domain portion and an RSG targeting portion having a sequence of GGHRRGSRPSGAERRRRAAAA (SEQ ID NO: 28). This ligand may be custom synthesized from a commercial vendor. Alternatively, the ligand could be produced by any suitable-phase coupling, solid-phase synthesis, chemoselective peptide ligation, cellular expression methods, or cell culture synthesis methods. Other examples of ligands in accordance with the present invention comprise a GGH metal binding domain linked to a Rev targeting domain by x linker amino acid residues, where x=0, 1, 2, and so on. The x linker amino acid may be any appropriate amino acid such as G. The ligands have sequences comprising GGHTRQARRNRRRRWR-ERQR (SEQ ID NO: 29) or GGHGTRQARRNRRRRWR-ERQR (SEQ ID NO: 30) or GGHGGTRQARRNRRRRWR-ERQR (SEQ ID NO: 31). The ligands may be made in accordance with the methods discussed above. In yet another example, the ligands may comprise the GGH, KGHK (SEQ ID NO: 1), VIHN (SEQ ID NO: 4), and YIHPF (SEQ ID NO: 5) metal binding peptides that may also have targeting properties. The ligands may comprise metalloligands as disclosed in U.S. Pat. No. 6,403,777.

It will be understood that the ligands of the present invention can be applied to the target in ligand or metalloligand form. For example, the ligands can enter a cell, subsequently bind a metal, and bind to and catalytically degrade or inactivate a target in the cell.

The ligands of the present invention are used in conjunction with a desired metal to form metal-ligand complexes. In one embodiment, the ligands of the present invention may exhibit a high affinity for a metal in at least one oxidation state, such as Kd<1 nM. In another embodiment, the ligands of the present invention may exhibit a high affinity for a desired metal in each bioavailable oxidation state. For example, the ligand may exhibit a high affinity for both Cu(II) and Cu(I).

The metal-ligand complexes of the present invention may be used to recognize and catalytically degrade (or inactivate) a target. The metal-ligand complexes may be utilized as drugs to destroy a drug target. The metal-ligand complexes may exhibit specificity to a desired target, and such specificity may reduce undesirable side effects when the ligands are employed as drugs. Examples of targets include, but are not limited to: nucleic acids such as DNA and RNA; metalloproteins; enzymes such as proteases; and receptors such as membrane proteins. For example, the target may comprise structured RNA molecules specific to or overexpressed in disease states such as cancer, viruses, bacteria, or other pathogens. The structured RNA may comprise IRES elements such as HIV TAR and HCV IRES. The structured RNA may comprise nuclear export sequences such as HIV RRE and NS2 in influenza, and the structured RNA may comprise genomes of RNA viruses or guide RNA in trypanosomes.

The target may comprise enzymes specific to viruses, bacteria, or other pathogens, and the target may be a polymerase. The target may comprise enzymes implicated in human diseases such as cancer, cardiovascular disease, and the like. For example, the enzymes may be proteases, angiogenic factors, enzymes in therapeutically relevant pathways such as hormone synthesis, vasoconstrictors, and fatty acid biosynthesis. The target may comprise non-enzymatic proteins such as structural proteins implicated in human disease or necessary for pathogen survival, division, toxicity, and the like. For example, the non-enzymatic proteins may comprise cell wall glycoproteins, amyloid plaques, and tubulin. The target may also comprise macromolecules that do not currently have a known function.

The targets may be selected in any suitable manner. For example, the target may be selected because it is implicated in human disease, it is specific to an organism or cell type, overexpressed in an organism or cell type, and/or because it has sites that may be modified by oxidation or hydrolysis. The target may be selected because it has known ligands that bind to the target, is validated as a drug target, has biological relevance, is selective, is specific, and/or displays relative abundance and feasibility of targeting. Additionally, the target may be selected because it is a known toxin or biohazard, and the ligand can be used for sterilization, sanitation, decontamination, or the like.

The metal-ligand complexes of the present invention may be used to target and inhibit a desired target, as in traditional drug design. Additionally, the metal-ligand complexes of the present invention may catalytically degrade or inactivate the target. For example, the metal-ligand complexes may catalytically degrade or inactivate the target by cleaving the target. This ability to catalytically degrade or inactivate the target may provide several advantages over traditional inhibition of a target. The metal-ligand complexes of the present invention may only need to be administered in substoichiometric or sub-saturating dosages because the ligand may have multi-turnover characteristics due to destruction of the target and regeneration of the original ligand complex. This potential for substoichiometric or sub-saturating dosages may decrease side-effects or toxicity of the ligands as administered to treat a specific disease state. Additionally, the destruction of the target may eliminate viral replication and ultimately eliminate the emergence of drug resistant viral strains. Additionally, the efficacy of the ligand against a target such as a viral target may not require efficient competitive binding against a natural ligand, because the target may be irreversibly destroyed at a low dose. In one embodiment, the dissociation constant of the metal-ligand complex to the target moiety may be equal to or lower than micromolar. The ligands of the present invention may be selected to display multi-turnover characteristics. For example, the ligands may be assayed to monitor the activity of the ligands in substoichiometric or sub-saturating amounts relative to a target.

The ligands of the present invention may be modified or selected to ensure cellular uptake of the ligands as needed. For example, the targeting domain may be selected to be arginine-rich such as Rev and Tat. Both the Rev and Tat peptides show cellular and nuclear penetrating capacity (*J. Biol. Chem.* 279 9208-9214, 2004; ibid 277, 2437-2443, 2002).

In another example, cell-penetrating peptides (CPP) may be used to enhance uptake of the ligand. The CPP may be used in addition to the targeting and metal binding domains or the CPP may be a portion of the targeting and/or metal binding domains. For example, Tat or a peptide derived from the antennapedia protein such as penetratin having a sequence of RQIKIWFQNRRMKWKK (SEQ ID NO: 32) may be used as the CPP. The amphipathicity or cationization of the ligand may be varied. For example, the linker composition may be changed or charges may be removed or added. Additionally, arginines may be added to enhance uptake similarly to how the Tat peptide is taken up by cells.

In another example, the ligand may be modified by attaching carbohydrates or receptor binding ligands for uptake via receptor-mediated endocytosis. The ligand may be selected such that it displays increased peptide stability and half-life. For example, the peptide bonds may be modified so that they cannot be cleaved by proteases, such as by changing the carbonyl to an alcohol or a carbonyl mimic while still maintaining properties (binding, etc.) important to that peptide or by replacement of nitrogen in peptide bonds with carbon. Additionally, the use of sequences recognized by proteases such as trypsin may be avoided. Further, the half-life can be manipulated by changing the water-solubility, i.e. increased water solubility will mean that the compound is excreted by the body faster.

The ligand may be delivered by using delivery vectors such as liposomes. The ligand may be packaged inside a liposomal delivery vesicle. The ligand may have a metal complex that promotes uptake. For example, a suitable ligand is shown in *Bioconjugate Chem.* 2004, 15(3), 475-481. Uptake may be improved by receptor based internalization. For example, the transferrin receptor is overexpressed on some cancer cells, and therapeutic agents have been conjugated to transferrin, such as doxorubicin as discussed in *J Drug Target.* 2000, 8, 305-318.

The ligands of the present invention may be selected for a specific target through the use of combinatorial chemistry, including phage display. In one example, a high-throughput rapid screen on a 96 well plate may be performed against labeled RNA. Various ligands may be reacted with labeled RNA in a 96-well plate, and the ligands that cause the largest change in fluorescence (either single fluorophor labeling or a FRET response) may be screened further. Additionally, gels to screen for cleavage by a ligand may be used by loading a reaction with labeled RNA onto a gel and monitoring for the formation of new bands or loss of original RNA bands. Random screening of small peptide libraries for lead compounds for use in the ligands of the present invention may be performed. Frankel's cell culture system for optimizing binding to RNA may be utilized as outlined in *RNA.* 2003, 9, 252-261. Once a suitable ligand or ligand has been identified, it may be optimized in any suitable manner.

An ATCUN motif metal binding domain may be attached to RRE peptide sequences, such as the Rev and RSG sequences, at the N-terminus. The Arg/Lys rich Rev peptide lacks additional copper binding ligands. The N-terminal ATCUN motif will be joined to the Rev peptide through an amino acid linker (Xaa)$_x$ with x as 0, 1, 2 and so on. This linker will provide varying degrees of flexibility between the recognition and cleavage domains on the copper peptide complex, allowing both easier optimization and access to the target for metal-promoted cleavage chemistry.

Peptides may be obtained from commercial sources in a highly purified form. Typically the purity and authenticity of the sample will be verified by high resolution HPLC and mass spectrometry. Copper ion will be added and the metal-peptide complex further purified and characterized by high performance liquid chromatography ("HPLC") and mass spectrometry. The presence of Cu(II) can also be verified by optical spectroscopy (for example, Cu (II)-ATCUN has a typical $\lambda_{max}$=525 nm with $\epsilon$~100 M$^{-1}$ cm$^{-1}$). The copper peptide complexes will be thoroughly characterized by optical spectroscopy to evaluate the ligand set around the metal, by circular dichroism to verify the retention of secondary structure by the peptide, and electrochemically to evaluate the redox chemistry of the metal center.

A 34-mer RNA containing the core HIV RRE RNA stem-loop motif may be commercially obtained in a highly purified form. Cleavage specificity by the copper peptide complexes will be evaluated by high-resolution gel electrophoresis of the reaction mixtures. Staining by the SYBR fluorescent dye to provide for facile visualization of product RNA bands may be established. The reactivity of the complexes will be determined by monitoring the time-course of the reaction following quantitation of the product bands at a number of selected time intervals.

The 34-mer RNA will also be 5'-labeled or 3'-labeled or double end labeled with one or two fluorescein conjugates to provide a fluorescent probe for real time kinetic measurements of copper peptide cleavage chemistry and a convenient probe for determination of binding affinities for the ATCUN extended peptides. To evaluate the reaction pathway (hydrolytic or oxidative) reactions will be performed under hydrolytic conditions in the absence of external reductant, and following the addition of ascorbate as an electron donor to promote formation of reactive oxygen species capable of mediating oxidative scission of the RNA backbone. HPLC in combination with high-resolution mass spectrometry will be used to separate and characterize reaction products and provide insight on the molecular pathway for degradation.

Selected ligands may be evaluated for inhibitory effects against HIV-1 Rev in a cell-based assay for Rev function. This assay uses the pDM128 Rev reporter plasmid. The pDM128 plasmid is modified by replacing the chloramphenicol acetyltransferase coding sequence with that of *Renilla* Luciferase. HeLa cells engineered to express HIV-1 Rev and Firefly Luciferase are subsequently transfected with the modified pDM128 plasmid to generate a cell line in which *Renilla* Luciferase expression is dependent upon Rev function. In contrast, Firefly Luciferase expression in this cell line is independent of Rev function and is used to assay for non-specific or toxic compounds. Using this system, compounds that inhibit Rev function are identified by their ability to reduce the expression of *Renilla* Luciferase with no effect on the expression of Firefly Luciferase. Assays are performed in 96 well format by plating cells (2×10$^4$/well) in the presence of the test compound (triplicate wells) and incubating 24-48 hours. Luciferase expression levels are subsequently determined using Dual-Luciferase assay reagents (Promega) following the manufacturer's instructions. The present invention also includes pharmaceutical compositions comprising these ligands, and at least one pharmaceutically acceptable excipient. Any of the inventive ligands, employed in the methods of the invention, can be administered orally, parenterally (IV, IM, depot-IM, SQ, and depot-SQ), sublingually, intranasally (inhalation), intrathecally, topically, or rectally. Dosage forms known to those of skill in the art are suitable for delivery of the inventive ligands employed in the methods of the invention.

Compositions are provided that contain therapeutically effective amounts of the inventive ligands employed in the methods of the invention. The ligands can be formulated into suitable pharmaceutical preparations such as tablets, capsules, or elixirs for oral administration or in sterile solutions or suspensions for parenteral administration. The ligands described herein can be formulated into pharmaceutical compositions using techniques and procedures well known in the art.

The inventive ligand or mixture of inventive ligands employed in the methods of the present inventions, or a physiologically acceptable salt or ester is compounded with a physiologically acceptable vehicle, carrier, excipient, binder, preservative, stabilizer, flavor, etc., in a unit dosage form as called for by accepted pharmaceutical practice. The amount of active substance in those compositions or preparations is such that a suitable dosage is obtained. The compositions can be formulated in a unit dosage form. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

To prepare compositions, one or more inventive ligands employed in the methods of the invention are mixed with a suitable pharmaceutically acceptable carrier. Upon mixing or addition of the ligand(s), the resulting mixture may be a solution, suspension, emulsion, or the like. Liposomal suspensions may also be used as pharmaceutically acceptable carriers. These may be prepared according to methods known to those skilled in the art. The form of the resulting mixture depends upon a number of factors, including the intended mode of administration and the solubility of the compound in the selected carrier or vehicle. The effective concentration is sufficient for lessening or ameliorating at least one symptom of the disease, disorder, or condition treated and may be empirically determined.

Pharmaceutical carriers or vehicles suitable for administration of the ligands provided herein include any such carriers suitable for the particular mode of administration. In addition, the active materials can also be mixed with other active materials that do not impair the desired action, or with materials that supplement the desired action, or have another action. The ligands may be formulated as the sole pharmaceutically active ingredient in the composition or may be combined with other active ingredients.

Where the ligands exhibit insufficient solubility, methods for solubilizing may be used. Such methods are known and include, but are not limited to, using co-solvents such as dimethylsulfoxide (DMSO), using surfactants such as TWEEN, and dissolution in aqueous sodium bicarbonate. Derivatives of the ligands, such as salts or prodrugs, may also be used in formulating effective pharmaceutical compositions.

The concentration of the ligand is effective for delivery of an amount upon administration that lessens or ameliorates at least one symptom of the disorder for which the ligand is administered. Typically, the compositions are formulated for single dosage administration.

The inventive ligands employed in the methods of the invention may be prepared with carriers that protect them against rapid elimination from the body, such as time-release formulations or coatings. Such carriers include controlled release formulations, such as, but not limited to, microencapsulated delivery systems. The active ligand can be included in the pharmaceutically acceptable carrier in an amount sufficient to exert a therapeutically useful effect in the absence of undesirable side effects on the patient treated. The therapeutically effective concentration may be determined empirically by testing the ligands in known in vitro and in vivo model systems for the treated disorder.

The ligands and compositions of the invention can be enclosed in multiple or single dose containers. The enclosed ligands and compositions can be provided in kits, for example, including component parts that can be assembled for use. For example, an inventive ligand in lyophilized form and a suitable diluent may be provided as separated components for combination prior to use. A kit may include an inventive ligand and a second therapeutic agent for co-administration. The inventive ligand and second therapeutic agent may be provided as separate component parts. A kit may include a plurality of containers, each container holding one or more unit dose of the inventive ligand employed in the method of the invention. The containers can be adapted for the desired mode of administration, including, but not limited to tablets, gel capsules, sustained-release capsules, and the like for oral administration; depot products, pre-filled syringes, ampoules, vials, and the like for parenteral administration; and patches, medipads, creams, and the like for topical administration.

The concentration of active inventive ligand in the drug composition will depend on absorption, inactivation, and excretion rates of the active compound, the dosage schedule, and amount administered as well as other factors known to those of skill in the art.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions.

If oral administration is desired, the ligand can be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active ligand or ligands can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The ligands can also be administered as a component of an elixir, suspension, syrup, wafer, chewing gum or the like. A syrup may contain, in addition to the active ligands, sucrose as a sweetening agent and certain preservatives, dyes and colorings, and flavors.

Solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerin, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include, but are not limited to, physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers. These may be prepared according to methods known in the art.

The inventive ligands may be prepared with carriers that protect the compound against rapid elimination from the body, such as time-release formulations or coatings. Such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those skilled in the art.

Ligands employed in the methods of the invention may be administered enterally or parenterally. When administered orally, compounds employed in the methods of the invention can be administered in usual dosage forms for oral administration as is well known to those skilled in the art. These dosage forms include the usual solid unit dosage forms of tablets and capsules as well as liquid dosage forms such as solutions, suspensions, and elixirs. When the solid dosage forms are used, they can be of the sustained release type so that the compounds employed in the methods of the invention need to be administered only once or twice daily.

The oral dosage forms can be administered to the patient 1, 2, 3, or 4 times daily. The inventive ligands employed in the methods of the invention can be administered either three or fewer times, or even once or twice daily. Hence, the inventive compounds employed in the methods of the invention be administered in oral dosage form. Whatever oral dosage form is used, they can be designed so as to protect the compounds employed in the methods of the invention from the acidic environment of the stomach. Enteric coated tablets are well known to those skilled in the art. In addition, capsules filled with small spheres each coated to protect from the acidic stomach, are also well known to those skilled in the art.

The inventive ligands employed in the methods of the invention may also be delivered in nanocrystal dispersion formulations. Preparation of such formulations is described, for example, in U.S. Pat. No. 5,145,684, the entire contents of which is incorporated by reference. Nanocrystalline dispersions of HIV protease inhibitors and their method of use are described in U.S. Pat. No. 6,045,829, the entire contents of which is incorporated by reference. The nanocrystalline formulations typically afford greater bioavailability of drug compounds.

The terms "therapeutically effective amount" and "therapeutically effective period of time" are used to denote treatments at dosages and for periods of time effective to reduce at least one symptom of the disorder for which it is administered or to produce the desired effect. As noted above, such administration can be parenteral, oral, sublingual, transdermal, topical, intranasal, or intrarectal.

It should be apparent to one skilled in the art that the exact dosage and frequency of administration will depend on the particular ligands employed in the methods of the invention administered, the particular condition being treated, the severity of the condition being treated, the age, weight, general physical condition of the particular patient, and other medication the individual may be taking as is well known to administering physicians who are skilled in this art.

Example 1

Angiotensin converting enzyme (ACE, peptidyl dipeptidase A; EC 3.4.15.1) is a zinc-containing metalloenzyme associated with the plasma membrane of epithelial and endothelial cells. It is exposed at the extracellular surface and functions as a dicarboxypeptidase, converting the natural peptide substrate angiotensin I (Ang I) to angiotensin II (Ang II), (FIG. 4a) a potent vasopressor. It also converts the vasodilator peptide bradykinin to an inactive form, thus playing an important role in blood pressure regulation.

The potency of the peptides GlyGlyHis (GGH), LysGlyHisLys (KGHK, SEQ ID NO: 1), TyrIleHisProPhe (YIHPF, SEQ ID NO: 5), and their corresponding $Cu^{2+}$ complexes toward ACE inhibition was determined by establishing a dose-dependant inhibition curve under equilibrium conditions. The experiments were carried out using the following protocols. All experiments were performed in triplicate and the results show the mean values of each activity determination.

Enzyme.

A recombinant isoform of human Angiotensin Converting Enzyme (rhACE) corresponding to the ectodomain somatic ACE was obtained from R&D systems Inc., supplied as a 0.2 µm filtered solution in 12.5 mM Tris, 75 mM NaCl, 0.5 µM ZnC12, pH 7.5 and 40% glycerol at a concentration of 0.434 mg/mL. Working stock solutions were made by diluting aliquots of the supplied stock into buffer (50 mM HEPES containing 300 mM NaCl and 10 µM $ZnCl_2$, pH 7.4). Fresh stocks were made prior to each experiment.

Peptides and Metallopeptides.

Peptides containing histidine as a third residue (ATCUN motifs), such as glycylglycylhistine (GGH) (BACHEM Bioscience), lysylglycylhistidyllysine (KGHK, SEQ ID NO: 1) (BACHEM Bioscience), and tyrosylisoleusylhidstudylprolylphenylalanine (YIHPF Angiotensin II 4-8, SEQ ID NO: 5) (Phoenix Pharmaceutical Inc.) were chosen for the study. Peptide stock solutions were prepared in de-ionized water and complexes with divalent copper were formed in 1:1.2 metal to peptide ratio in 50 mM HEPES buffer (pH 7.4) using $CuSO_4 \cdot 5H_2O$ as the source of the metal ion. The concentrations of the $Cu^{2+}$ peptide complexes were determined spectrophotometrically, using $\epsilon_{528\ nm} \sim 108\ M^{-1}cm^{-1}$ for [GGH-Cu]$^-$ and $\sim 85\ M^{-1}cm^{-1}$ for [KGHK-Cu]$^+$ (SEQ ID NO: 1), respectively.

Enzyme Assays.

Recombinant human ACE activity was assayed (final volume of 100 µl) at 37° C. in a buffer consisting of 50 mM HEPES containing 300 mM NaCl and 10 µM $ZnCl_2$ (pH 7.4) with 10 µM internally quenched fluorogenic peptide substrate, Mca-Arg-Pro-Pro-Gly-Phe-Ser-Ala-Phe-Lys(Dnp)-OH (SEQ ID NO: 2) (R&D Systems Inc.) and 1 nM (13.1 ng) rhACE. Reactions were run in the wells of polystyrene 96-well microplates (PS white, Porvair). The time-dependent increase in fluorescence following cleavage of the peptide substrate was monitored (relative fluorescence units/min, RFU/min). Fluorescence change was typically measured for 30 min with a Perkin Elmer Luminescence Spectrophotometer LS50B equipped with a fluorescence microplate reader (Perkin Elmer) at 37° C. using PE applications FL winlab software with excitation and emission wavelengths set at 320 and 405 nm, respectively. Optimum substrate concentration was identified by incubating the enzyme with 5 to 50 µM substrate.

Determination of Kinetic Constants.

Determination of $K_m$ and $V_{max}$ values was carried out using the fluorescence assay described above. Reactions were carried out for 30 min at 37° C. Initial rates for the hydrolysis of substrate ($V_o$) were determined by following the change in fluorescence (relative fluorescence units/min, RFU/min), plotted as a function of substrate concentration ([S]) and fit to the Michaelis-Menten equation $V_o = V_{max}[S]/([S]+K_m)$, using Origin software (Microcal) to determine $K_m$. Substrate concentration was varied from 0 to 20 µM (FIGS. 5-8.).

Determination of $IC_{50}$ values for rhACE inhibitors using, Mca-Arg-Pro-Pro-Gly-Phe-Ser-Ala-Phe-Lys(Dnp)-OH substrate (SEQ ID NO: 2).

Reaction mixtures (100 µl) contained 50 mM HEPES buffer, 300 mM NaCl and 10 µM $ZnCl_2$ (pH 7.4), 10 µM substrate and 1 nM (13.1 ng) rhACE. Concentrations of GGH, KGHK (SEQ ID NO: 1), YIHPF (SEQ ID NO: 5), $Cu^{2+}$, Cu(GGH)$^-$, Cu(KGHK)$^+$ (SEQ ID NO: 1), Cu(YIHPF)$^-$ (SEQ ID NO: 5), were varied from 0 to 100 µM. Prior to the start of the enzymatic reaction (by addition of substrate) the inhibitors were pre-incubated with the enzyme for 45 min. Reactions were run in the wells of polystyrene 96-well microplates (Porvair) as described previously. Fluorescence was measured for 70 min. and the background rate determined for samples containing no rhACE was subtracted from all reactions to calculate the initial rates in RFU/min. Initial rate data were plotted as percentage activity, relative to uninhibited control reactions, as a function of inhibitor concentration (FIGS. 9-12).

Determination of the Type of Inhibition.

Reaction mixtures (100 µl) contained 50 mM HEPES buffer, 300 mM NaCl, 10 µM $ZnCl_2$ (pH 7.4) and 1 nM (13.1 ng) rhACE. Two sets of reactions were performed at distinct substrate concentration (5 and 10 µM) with varying concentrations of inhibitor (0 to 20 µM). Prior to the start of the enzymatic reaction (by addition of substrate) the inhibitors were pre-incubated with the enzyme for 45 min. Reactions were run in the wells of polystyrene 96-well microplates (Porvair). Fluorescence change was measured for 30 min as described previously. Initial rate data were plotted versus inhibitor concentration and a Dixon plot (inverse of initial velocity versus inhibitor concentration) was generated using Origin (Microcal).

Determination of Inhibition Constants.

For the competitive inhibitors the enzyme-inhibitor dissociation constant ($K_I$) was determined by graphical methods by use of a Dixon plot, as well as by the equation below, where $IC_{50}$, [S] and $K_m$ have units of molar concentration. $K_I=IC_{50}/(1+[S]/K_m)$.

Determination of the Inhibition Mechanism under Oxidative Reaction Conditions.

Enzymatic reactions performed in the presence of dioxygen and ascorbate are defined as oxidative conditions, while all other reactions described herein that contained no ascorbate are defined as hydrolytic. Reaction mixtures (100 μl) contained 50 mM HEPES buffer, 300 mM NaCl, 10 μM $ZnCl_2$ (pH 7.4), 10 μM ascorbate (L-ascorbic acid, prepared in deionized water) and 1 nM (13.1 ng) rhACE. The concentration of inhibitor was set at $K_1$. Prior to the start of the enzymatic reaction (either by addition of substrate or the enzyme) the inhibitors were pre-incubated with the enzyme for 45 min. Two sets of reactions were run in the wells of polystyrene 96-well microplates (Porvair) and fluorescence change (relative fluorescence units/min, RFU/min) was measured for 30 min as described previously.

Figure 13:
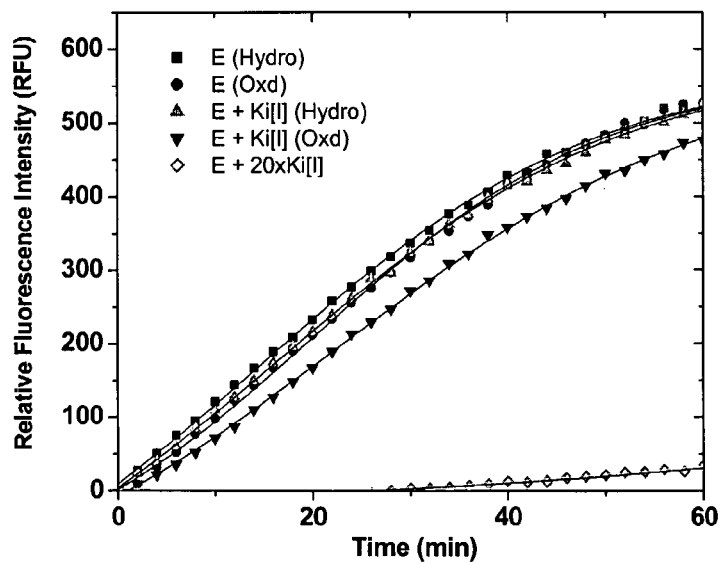
FIG. 13 is a plot of RFU with time (min) under various experimental conditions (progress curve), where E(hydro) is the hydrolytic control, E(Oxd) is the oxidative control, E+K(I)(Hydro) contains the inhibitor at a concentration of 4 μM under hydrolytic conditions, E+K(I)(Oxd) contains the inhibitor at a concentration of $K_1$ under oxidative conditions, and E+20xK(I)) contains the inhibitor at a concentration 20-fold higher than $K_1$ under oxidative conditions.
Figure 14:
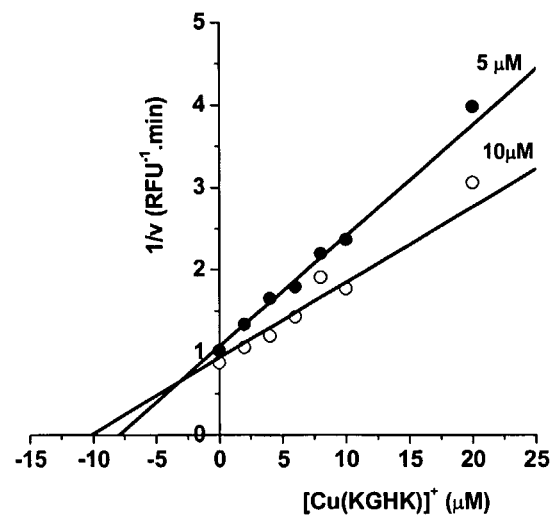
FIG. 14 is a Dixon plot showing competitive inhibition, where substrate (Mca-Arg-Pro-Pro-Gly-Phe-Ser-Ala-Phe-Lys(Dnp)-OH, SEQ ID NO:2) concentrations of 5 and 10 μM were used (KGHK is disclosed as SEQ ID NO: 1).

Set I: Monitoring the progress curve for the enzymatic reaction under oxidative conditions: Following prior pre-incubation of the enzyme with the inhibitor, the enzymatic reaction was initiated by simultaneous addition of the substrate and ascorbate, and the progress of the reaction monitored by formation of product as reflected by the observed change of fluorescence. The initial velocity ($V_o$), obtained from the progress curve in the presence and absence of the inhibitor, was plotted versus time as described. Respective control reactions had either ascorbate present or absent (FIG. 13).

Set II: Enzyme deactivation under oxidative conditions in the presence and absence of inhibitor: To obtain a true rate of enzyme deactivation by the inhibitor under oxidative conditions the enzyme was pre-incubated with the inhibitor for 45 min. Ascorbate was added, followed by a preincubation time, and aliquots of the reaction mixture were taken at various time intervals and the residual enzyme activity estimated using the 96-well plate assay described previously. Initial velocity ($V_o$) obtained in the presence and absence of inhibitor was plotted as a function of time and fitted to the first-order rate equation to obtain $k_s$.

Figure 11:
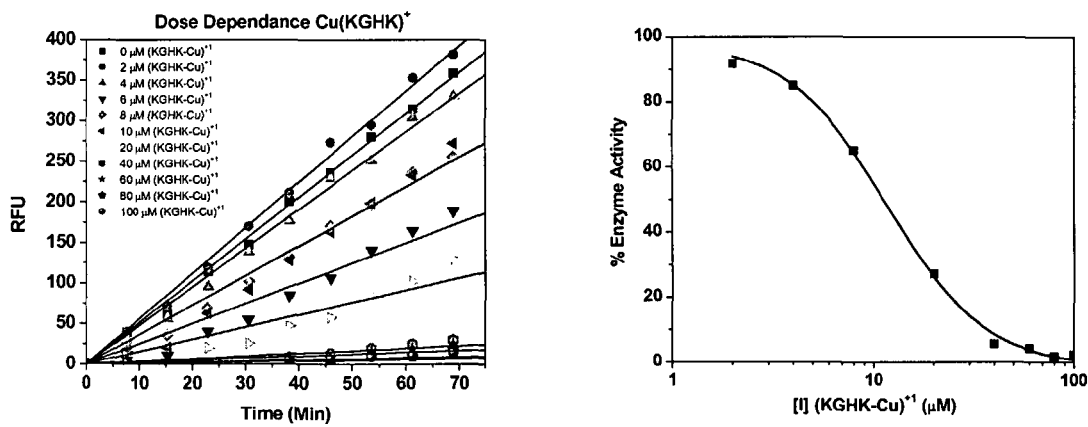
Figure 12:
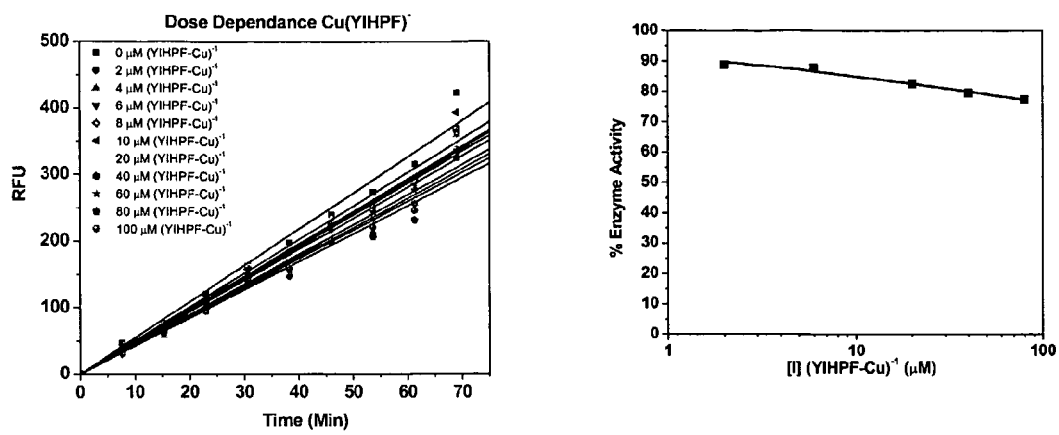

Results. The measured $IC_{50}$ values for all of the metal-free peptides, and the copper complexes [GGH-Cu]$^-$ and [YIHPF-Cu]$^-$ (SEQ ID NO: 5), were found to be >100 μM, however, the $IC_{50}$ for [KGHK-Cu]$^+$ (SEQ ID NO: 1) was determined to be 11 μM. A pre-incubation time of at least 45 min significantly enhanced the inhibitory effect of the metallopeptides, suggesting slow binding to the enzyme active site. Under such pre-incubation conditions, and under hydrolytic conditions (no ascorbate present), the $Cu^{2+}$-peptide [KGHK-Cu]$^+$ (SEQ ID NO: 1) was found to be a competitive inhibitor ($K_I\sim4$ μM) (FIG. 11).

Figure 15:
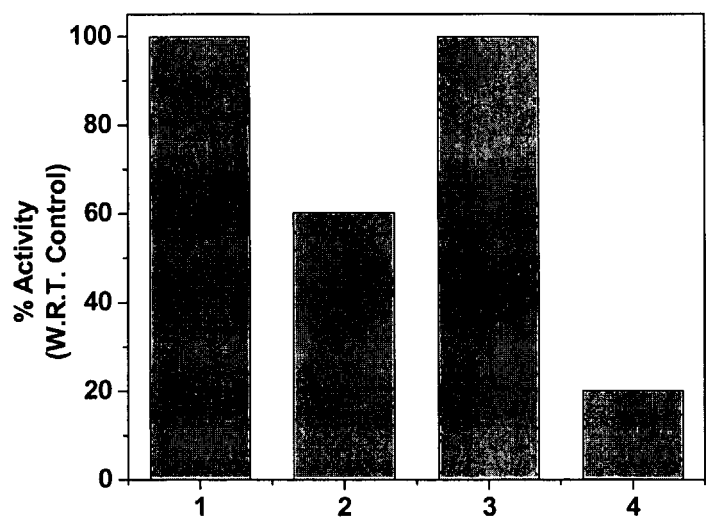
FIG. 15 is a comparison of ACE inhibition activity for [KGHK-Cu]$^+$ (SEQ ID NO: 1) ($IC_{50}$=11 μM) evaluated under a variety of experimental conditions. The reaction solution contained 10 μM substrate (Mca-Arg-Pro-Pro-Gly-Phe-Ser-Ala-Phe-Lys(Dnp)-OH, SEQ ID NO: 2), 10 μM $ZnCl_2$ in 50 mM HEPES (pH 7.4) buffer with 300 mM NaCl and 1 nM ACE. (1) Hydrolytic control with no inhibitor and no ascorbate. (2) 4 μM [KGHK-Cu]$^+$ (SEQ ID NO: 1), no ascorbate. (3) Oxidative control with 10 μM ascorbate. (4) 4 μM [KGHK-Cu]$^+$ (SEQ ID NO: 1), and 10 μM ascorbate. The enzyme was pre-incubated for 45 min with the metallopeptide. Relative activity was measured after 30 min using a fixed time assay under the conditions of initial velocity measurements.

A dramatic change in enzyme inactivation was observed, relative to the inhibitor metallopeptide, following a switch from hydrolytic to oxidative conditions. Employing the peptide complex [KGHK-Cu]$^+$ (SEQ ID NO: 1) at sub-saturating concentrations ($K_I$) the inhibitory activity of [KGHK-Cu]$^+$ (SEQ ID NO: 1) was enhanced several fold in the presence of a two fold excess of ascorbate and dioxygen, relative to inhibition under hydrolytic conditions (FIG. 15).

Figure 16:
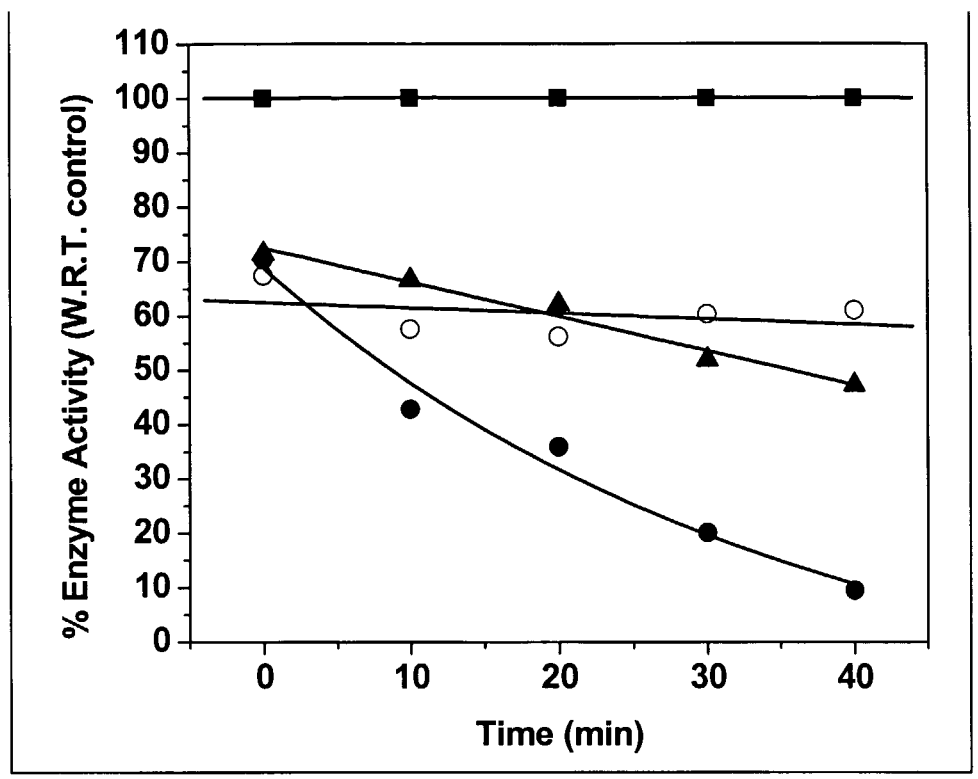
FIG. 16. Enzyme activity was determined at the given time intervals by taking aliquots of enzyme and determining the activity under initial velocity conditions with 10 μM substrate (Mca-Arg-Pro-Pro-Gly-Phe-Ser-Ala-Phe-Lys(Dnp)-OH, SEQ ID NO: 2) and 10 μM $ZnCl_2$ in 50 mM HEPES (pH 7.4) containing 300 mM NaCl, and 1 nM ACE. Conditions included (■) no inhibitor 10 μM ascorbate; (●) with [KGHK-Cu]$^+$ (SEQ ID NO: 1) (4.4 μM), 10 μM ascorbate; (○) with [KGHK-Cu]$^+$ (SEQ ID NO: 1) (4.4 μM), no ascorbate; and (▲) with $Cu^{2+}$ (aq) (4 μM), 10 μM ascorbate.

The [KGHK-Cu]$^+$ (SEQ ID NO: 1)-mediated catalytic inactivation of ACE was followed by monitoring the progress curve for inactivation of recombinant human ACE by [KGHK-Cu]$^+$ (SEQ ID NO: 1) at a sub-saturating concentration (4 μM) of complex under both hydrolytic and oxidative conditions (FIG. 16). Under hydrolytic conditions, inhibition of ACE by [KGHK-Cu]$^+$ (SEQ ID NO: 1) is proportional to the inhibitor concentration. However, in the presence of ascorbate (a two-fold excess relative to that of inhibitor) enzyme deactivation was achieved to a significantly greater extent, relative to the inhibitor's initial concentration, supporting catalytic multi-turnover inactivation. In the presence of dioxygen and excess ascorbate, free $Cu^{2+}$(aq) is transiently reduced to $Cu^+$(aq) and exhibits a lower inhibition profile than that of free $Cu^{2+}$(aq) under hydrolytic conditions, most likely resulting from the weaker binding of $Cu^+$(aq) by the enzyme active site. Efficient multi-turnover inactivation of ACE at sub-saturating concentrations of [KGHK-Cu]$^+$ (SEQ ID NO: 1) was achieved under oxidative conditions and kinetic parameters obtained by initial velocity measurements (FIG. 16) furnished a catalytic rate constant, $k_{obs}\sim2.86\times10^{-2}$ min$^{-1}$ for enzyme deactivation. Accordingly, this family of metallopeptides can act not only as classical competitive inhibitors of enzyme activity, but also show the potential for irreversible catalytic inactivation of enzyme function at sub-saturating concentrations.

Example 2

The RRE RNA cleavage chemistry by copper-Rev1 peptide (sequence: GGHTRQARRNRRRRWRERQR (SEQ ID NO: 29), where underlined part indicates Rev peptide sequence) complex was studied in vitro using 5'-fluorescein end labeled RNA in the presence and absence of mild reducing agents such as ascorbate. The experiments were performed using the following protocols.

General Materials.

The peptides used in this study were purchased from Genemed Synthesis Inc. RRE RNA with or without 5' fluorescein labeling was purchased from Dharmacon RNA Technologies. All materials were prepared under RNase free conditions as previously described[1] or purchased in the highest commercially available grades. Unless stated, all other reagents used in this research were obtained from Sigma chemical Co.

Synthesis and Characterization.

A solution of 2.2 mM peptide in 50 mM Hepes buffer (pH=7.4) was mixed with 2 mM $CuCl_2$ in 50 mM Hepes buffer solution in 1:1 v:v ratio. This yielded a 1.1:1 peptide to copper ratio, and so there was no free $Cu^{2+}$ (aq) ion in the cleavage reaction mixture. The resulting solution was mixed at room temperature for ~30 min, resulting in a stable light reddish-purple solution that displayed a UV-vis spectrum typical of Cu-ATCUN complexes. Samples were maintained at 4° C. and concentrations and stabilities of the Cu-peptide complexes were routinely checked prior to use. A Tris buffer system can also be used without significant change.

Fluorescence Spectroscopy

Figure 17:
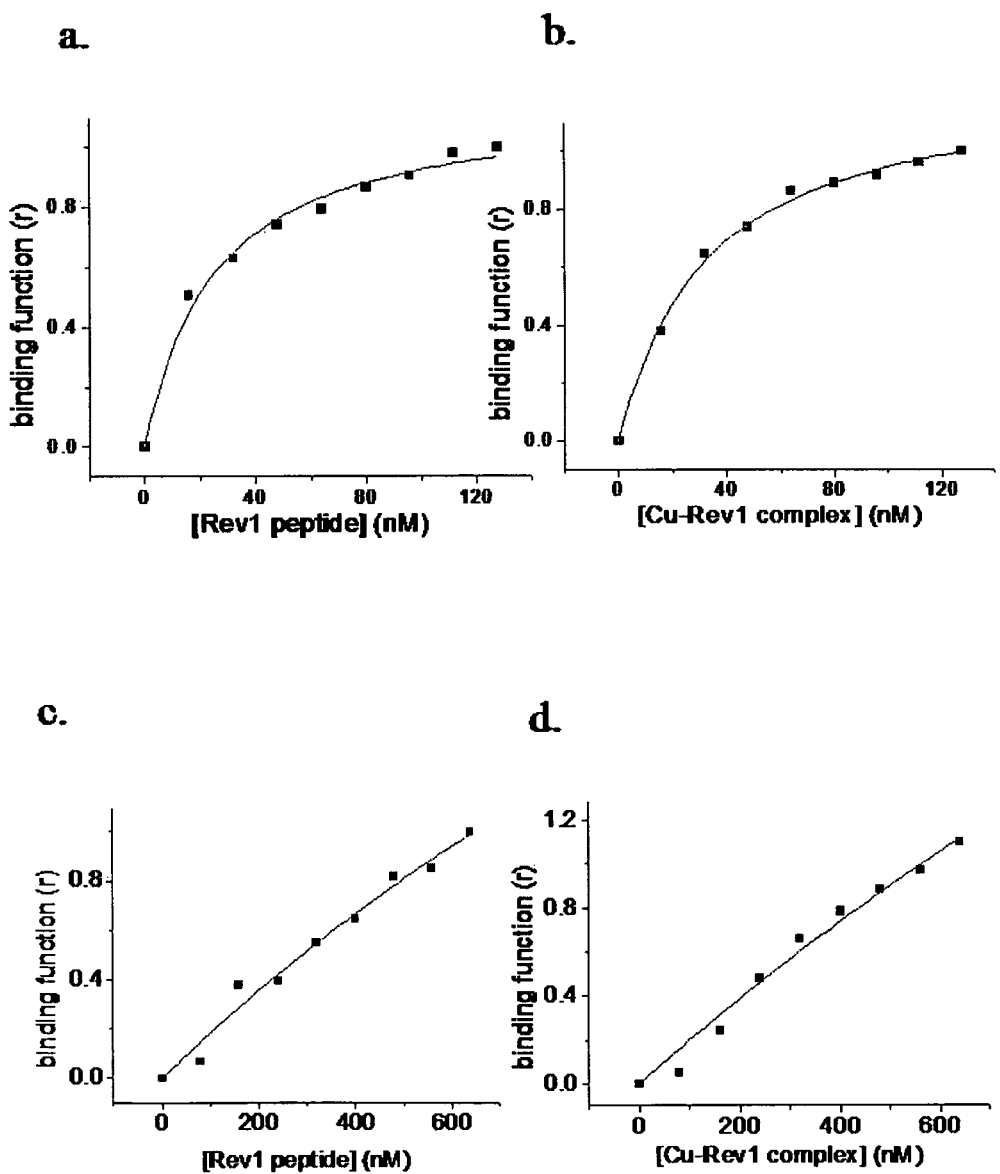
FIG. 17 illustrates the determination of $K_D$'s for Rev1 peptide and Cu-Rev1 complex formation with RRE RNA. Binding specificity was evaluated against 5' FL-labeled HIV TAR RNA. The $K_D$ of RRE and Rev1 binding is around 30 nM (*a*), while $K_D$ of RRE and Cu-Rev1 complex binding is around 35 nM (*b*). These numbers are consistent with the $K_D$ measured for RRE RNA and native Rev peptide lacking the ATCUN motif, which means adding GGH at the N-terminus and binding Cu do not influence the binding. (*c, d*) The binding of Rev1 or Cu-Rev-1 complex to TAR RNA is much looser, $K_D$~5 μM, which reflected their binding specificity toward RRE RNA.

A 6 nM solution of 5'-fluorescein labeled RRE RNA (molecular concentration) was prepared in 20 mM Hepes buffer, 100 mM NaCl, pH=7.4. A 1 μl aliquot of 5 μM (for RRE test) or 25 μM (for TAR test) peptide or Cu-peptide complex was measured in a 300 μl quartz cuvette at room temperature using a Perkin Elmer LS50B spectrofluorimeter, with excitation (slit=6) and emission (slit=6) wavelengths set at 490 nm and 515 nm, respectively. Dissociation constants were obtained by fitting fluorescence quenching date to a one site binding equation $r=Bx/(K_d+X)$ with binding function r (where $r=(y_t-y_0)/(y_{final}-y_{initial})$) versus x as peptide or Cu-peptide complex concentration (FIG. 17). The values for the dilution effect have already been subtracted from each point. Since our Cu-Rev1 complex has very little absorbance ($\epsilon_{515}$~30 $M^{-1}cm^{-1}$), the inner filter effect is negligible in this assay.

RNA Cleavage Studies with Gel Electrophoresis.

Figure 18:
FIG. 18 illustrates RNA cleavage of 5' FL-labeled RRE RNA by $Cu^{2+}$-Rev1 peptide complex with ascorbate. Lanes: 1. RRE RNA (~10 μM); 2, 3 RRE (~10)+$Cu^{2+}$-Rev1 peptide complex (10 μM)+ascorbate (100 μM); 4. RRE RNA (~10)+ascorbate (100 μM); 5. RRE (~10 μM)+Rev1 peptide (10 μM); 6. RRE (~10)+$Cu^{2+}$ (aq) (10 μM) 7. RRE (~10 μM)+$Cu^{2+}$ (aq) (10 μM)+ascorbate (100 μM). Reactions were incubated in 20 mM Hepes buffer, 100 mM NaCl, pH=7.4, for 3 hours at 37° C. Reaction products were separated on a 20% denaturing PAGE.

In general, RNA cleavage reactions were performed in 5 μA total volumes with 10 μM 5'-fluorescein labeled RRE RNA (molecular concentration), different concentrations of Cu-peptide complexes, and with or without excess amount of ascorbate in 20 mM Hepes buffer, 100 mM NaCl, pH=7.4 at 37° C. Control reactions were carried out at the same time (FIG. 18). The reactions were quenched with a loading buffer containing 8 M Urea and 0.5 M EDTA, but without dyes. The loading buffer with dyes was run in another lane to control the electrophoresis. The reaction samples were loaded onto either 15% or 20% polyacrylamide/8M urea denaturing gels (from American Bioanalytical) and electrophoresed at 300 V for 8 h. To avoid any influence on fluorescein, the reactions and gel eletrophoresis were performed in the dark. Each experiment was carried out at least in triplicate.

RNA Cleavage Products Characterized with Mass Spectrometry.

Figure 19:
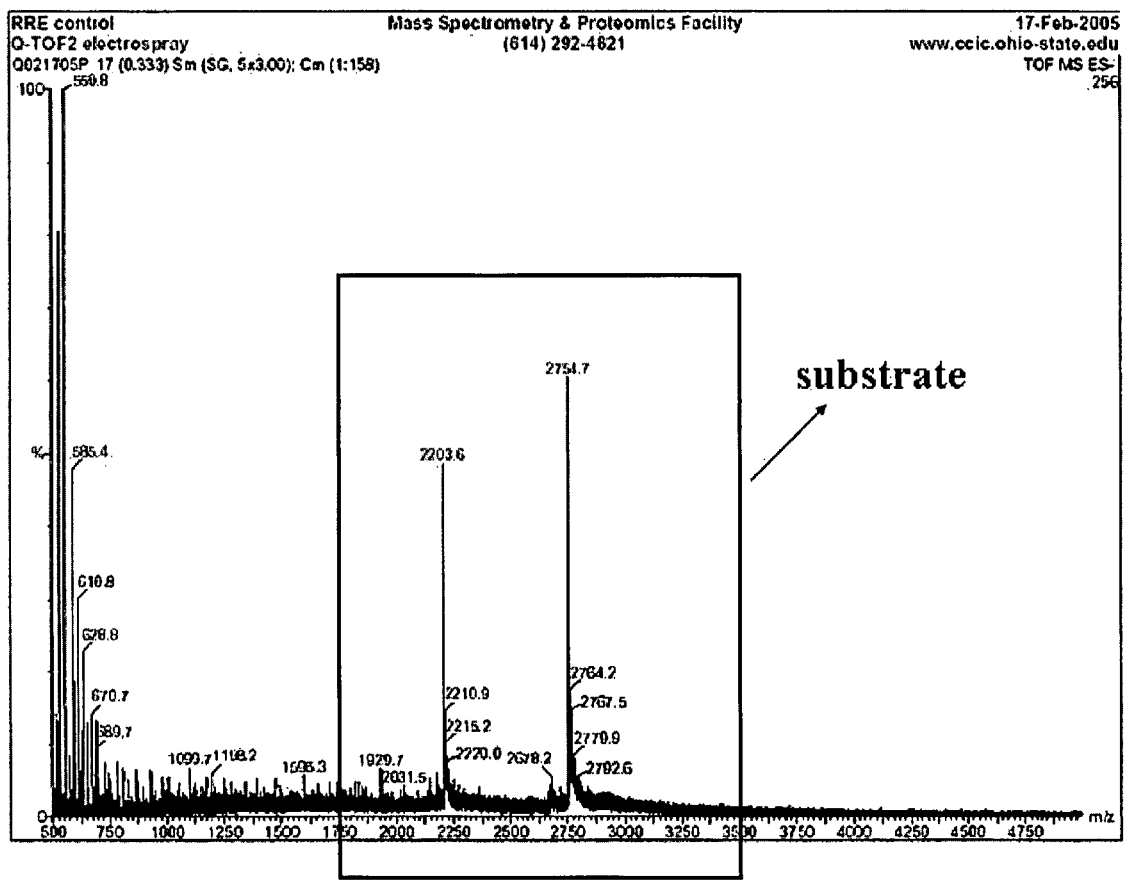
FIG. 19 illustrates RRE cleavage control reaction analyzed by mass spectrometry. Control reaction was performed under the same condition as reaction, but without Cu-peptide complex.
Figure 20:
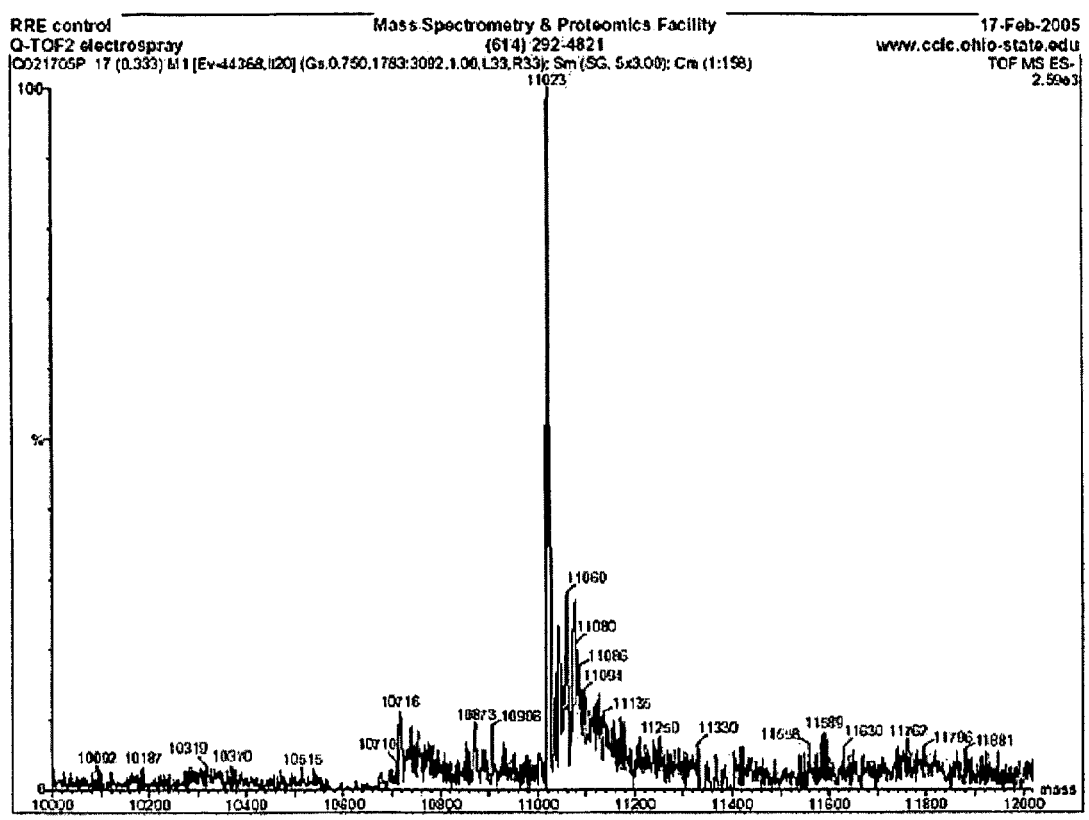
FIG. 20 illustrates RRE cleavage control (accurate mass of substrate RRE RNA after deconvolution).
Figure 21:
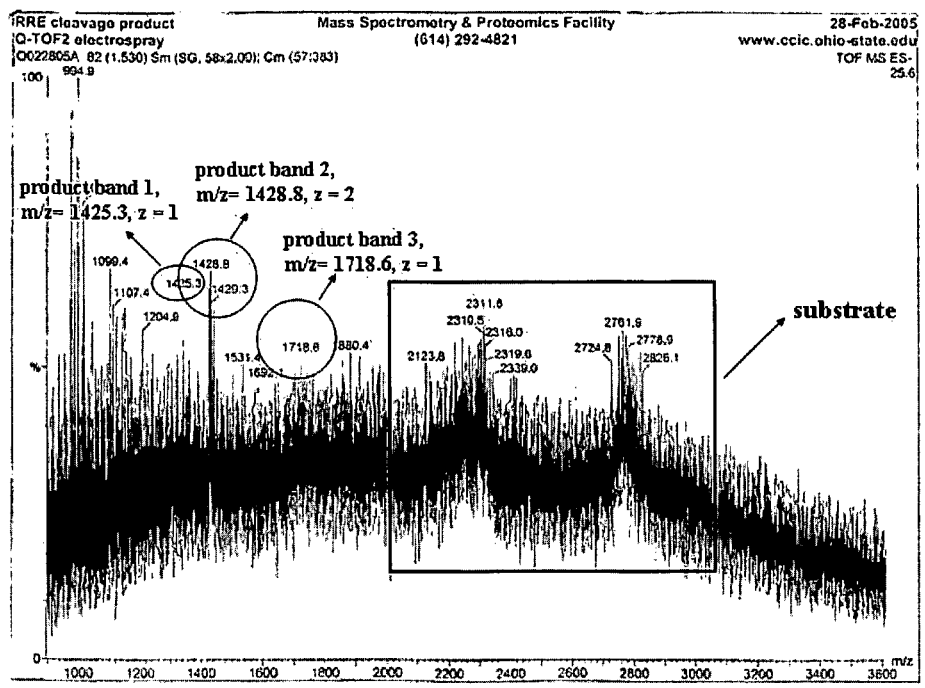
FIG. 21 illustrates the RRE cleavage reaction.
Figure 22:
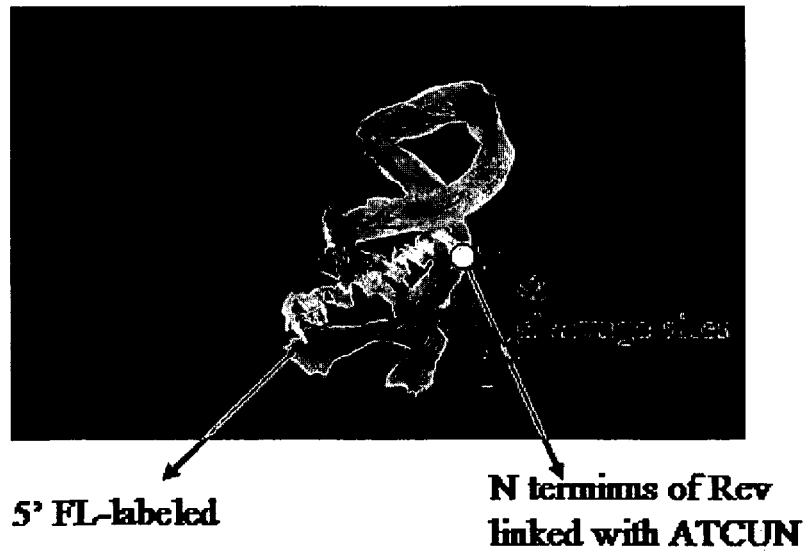
FIG. 22 illustrates Tertiary structures of RRE RNA and Rev peptide, showing the binding pocket and cleavage sites.

RNA cleavage reactions were performed in 40 μl total volumes with 100 μM unlabeled RRE RNA, 1:1 concentration ratio of Cu-peptide complex with 1 mM ascorbate in 20 mM Hepes buffer, 100 mM NaCl, pH=7.4 at 37° C. Control reactions were carried out with RRE RNA and ascorbate. ESI/MS was used to get the mass of the cleavage products. Electrospray ionization (ESI) experiments were performed on a Micromass Q-Tof™ II (Micromass, Wythenshawe, UK) mass spectrometer equipped with an orthogonal nanospray source from New Objective, Inc. (Woburn, Mass.) operated in negative ion mode. Sodium Iodide was used for mass calibration for a calibration range of m/z 500-3000. Salt buffers from the RNA samples were removed using ZipTips (Millipore, Billerica, Mass.) following recommended manufacturer protocols. The elutants from the ZipTip were used directly and infused into the electrospray source at a rate of 2 ml.min$^{-1}$. Optimal ESI conditions were: capillary voltage 3000 V, source temperature 110° C. and a cone voltage of 60 V. Q1 was set to optimally pass ions from m/z 500-3000 and all ions transmitted into the pusher region of the TOF analyzer were scanned over m/z (your ramge) with a 1 s integration time. Data was acquired in continuum mode until acceptable averaged data was obtained (10-15 minutes). ESI data was deconvoluted using MaxEnt I provided by Micromass (FIGS. 19-21) and the cleavage sites were assigned (FIG. 22).

Results.

Figure 23:
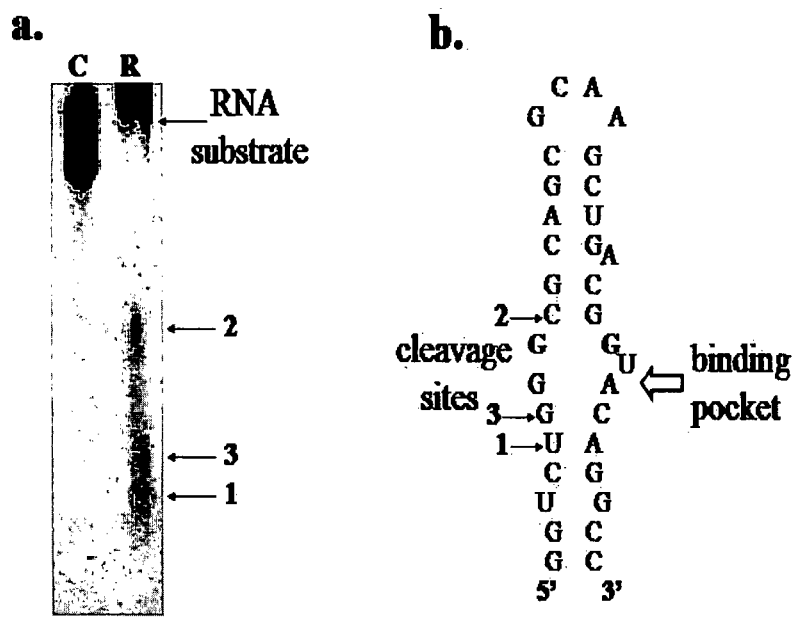
FIG. 23 (*a*) The cleavage reactions were analyzed with 8M urea denaturing 20% polyacrylamide gel eletrophoresis. C.

RRE was incubated at 37° C. for 6 hours with Cu-peptide complex, and the products of cleavage were separated on denaturing 15% or 20% polyacrylamide gel (FIG. 23a). Cleavage of RRE RNA was effective under stoichiometric condition (1:1 ratio of molecular concentrations of RRE RNA and Cu-peptide complex) in the presence of ascorbate. Two major (1, 2) and one minor (3) product bands were observed, where 20% PAGE gave better resolution.

The cleavage sites were assigned by mass spectrometry. In control reaction sample, only the substrate peak was recognized with accurate mass as 11023, while the calculated one is 11022.7. After reaction, the intensity of multiple charged peaks corresponding to RRE RNA substrate decreased, while new m/z ratio peaks appeared. The sizes of the products analyzed from the mass spectrometry result matched the products from PAGE. Combining both the PAGE and mass spectrometry data, RRE cleavage by the Cu-Rev1 peptide complex is not random, but rather three specific cleavage sites were observed along the binding pocket that are sterically approachable by the N-terminal Cu-GGH motif. Control reactions with either metal free peptide or free $Cu^{2+}$ (aq) were also carried out and analyzed by PAGE, respectively. In the presence of metal free peptide, no reaction was observed. In the case of free $Cu^{2+}$ (aq), RNA products were smeared on the gel as a result of random cleavage, and so no specific product was observed. The deviation between the accurate mass of cleavage products by mass spectrometry and the calculated mass of the hydrolytic products at the same sites indicated that oxidative cleavage is the pathway to cause the strand session.

The influence of $Mg^{2+}$(aq), which is important for the correct folding of some structured RNA, has also been evaluated. No significant difference was observed in $Mg^{2+}$ free reaction and reactions with various $Mg^{2+}$ concentrations. This observation is consistent with the current knowledge about RRE and Rev, where no special structural role for $Mg^{2+}$ has been discovered so far.

In the absence of ascorbate, the RRE RNA was still cleaved by Cu-Rev1 peptide complex under hydrolytic condition, but at a much slower pace than with the presence of ascorbate and with very limited extent (FIG. 24).

Example 3

Cleavage studies were performed using the following protocols. The protocols also apply to Examples 4, 5, and 6.

General Materials.

The GGH tripeptide and KGHK tetrapeptide (SEQ ID NO: 1) were purchased from Bachem Co., and used without further purification. Unless stated, all other reagents used in this research were obtained from Sigma Chemical Co.

Synthesis and Characterization.

A solution of 1 mM peptide in 10 mM Tris buffer (pH=7.4) was mixed with 0.8 mM $CuCl_2$ in 10 mM Tris buffer solution in 1:1 v:v ratio. This yielded a 1.25:1 peptide to copper ratio, and so there was effectively no free Cu (II) ion in the cleavage reaction mixture. The resulting solution was stirred at room temperature for ~30 min, resulting in a light reddish-purple solution that displayed a UV-vis spectrum similar to that observed previously. Samples were maintained at 4° C. and concentrations and stabilities of the [GGH-Cu]$^-$ and [KGHK-Cu]$^+$ (SEQ ID NO: 1) complexes were routinely verified prior to use.

DNA Cleavage Studies.

Plasmid pUC19 (2686 bp) was purchased from New England Biolabs Inc. The plasmid was transformed into DH5α competent cells, amplified, and pure plasmid isolated using QIAGEN protocols. Fresh plasmid DNA (over 90-95% supercoiled) was prepared before each experiment to avoid contamination by any other form of plasmid DNA. In general, DNA cleavage experiments were performed with 50 μM base pair concentration of pUC19, 25 μM Cu-peptide, and 250 μM ascorbate in 10 mM Tris buffer, pH 7.4, at 37° C. A control reaction was carried out using the same conditions as the cleavage reaction, but lacking the Cu-peptide complex. The reactions were quenched with a loading buffer containing 0.5 M EDTA.

Electrophoresis.

Agarose gel electrophoresis (0.8%) containing ethidium bromide was performed under standard conditions. DNA samples were run on horizontal gels in 1×TAE buffer for 90 min at 120 mV.

Results.

[GGH-Cu]$^-$ was found to mediate the rapid degradation of supercoiled (form I) plasmid DNA to produce nicked (form II) plasmid DNA at concentrations as low as 10 μM in the presence of ascorbate, but not under hydrolytic conditions (lacking ascorbate). The spontaneous hydrolysis of DNA was not observed under these conditions. Consistent with previous observations, neither ascorbate nor [GGH-Cu]⁻ alone demonstrated any apparent cleavage activity. Subsequently, the DNA cleavage chemistry of [KGHK-Cu]⁺ (SEQ ID NO: 1) was evaluated, with good activity levels evident even at 10 µM concentration, and was also observed to degrade (or inactivate) DNA more rapidly than [GGH-Cu]⁻ (FIGS. 25 and 26). Linear DNA was formed in the [KGHK-Cu]⁺ (SEQ ID NO: 1) cleavage samples (FIG. 26), requiring two breaks on opposing strands within 10 bp of each other, whereas linear DNA was not found in samples following treatment with [GGH-Cu]⁻. A smear pattern was observed for DNA treated with $Cu^{2+}$(aq) and ascorbate, indicating a random pattern of scission reaction, which is consistent with prior observations.

Example 4

DNA Cleavage Quantitation

Quantitation of closed circular, nicked and linear DNA was made by densitometric analysis of ethidium bromide containing agarose gels. Quantitation was performed by fluorescence imaging by use of a Gel-Doc 1000 (BioRad) and data analysis with Multianalysis software (version 1.1) provided by the manufacturer using the volume quantitation method. In all cases, background fluorescence was subtracted by reference to a lane containing no DNA. A correction factor of 1.47 was used for supercoiled DNA, since the ability of ethidium bromide to intercalate into supercoiled DNA (form I) is decreased relative to nicked (form II) and linear DNA (form III). The fraction of each form of DNA was calculated by dividing the intensity of each band by the total intensities of all the bands in the lane. All results were obtained from experiments that were performed at least in triplicate.

Results.

Kinetic parameters underlying the DNA cleavage chemistry of [GGH-Cu]⁻ and [KGHK-Cu]⁺ (SEQ ID NO: 1) were determined by following the time-dependence of the reaction under pseudo first-order conditions ([DNA]=50 µM, [[GGH-Cu]⁻]=25 µM, [ascorbate]=250 µM). The loss of supercoiled DNA and increased levels of nicked and linear DNA were quantitated following gel electrophoresis as described in methods and materials. Typical results from this set of experiments are shown in FIGS. 25 and 26. Both [GGH-Cu]⁻ and [KGHK-Cu]⁺ (SEQ ID NO: 1) were found to mediate the cleavage of one strand of dsDNA in the initial stage of the reaction. Quantitative production of nicked plasmid DNA (form II) was observed within 28 min for [GGH-Cu]⁻ (FIG. 1A), and within 6 min for [KGHK-Cu]⁺ (SEQ ID NO: 1) (FIG. 26A, although no linear DNA was formed during this initial period). A slower subsequent nicking was then promoted by [KGHK-Cu]⁺ (SEQ ID NO: 1) that resulted in formation of linear DNA (form III).

The reaction profile for the [GGH-Cu]⁻ mediated reaction displayed approximately pseudo-first order kinetic behavior (FIG. 1B), with $k_{obs}$~0.07 min⁻¹ and $R^2$=0.95. The reaction profile for DNA treated with [KGHK-Cu]⁺ (SEQ ID NO: 1) was also fitted to a pseudo-first order reaction ($R^2$=0.99) with $k_{obs}$~0.14 min⁻¹ (FIG. 26B). For the gel shown in FIG. 26A, the last point in lane 10 was omitted from the graph in FIG. 26B, since the DNA had already begun to smear as a result of multiple cleavage events.

The influence of added ascorbate was maximal when the ratio of [ascorbate]/[GGH-Cu]⁻ was greater or equal to 10:1, and so a ratio of at least 10:1 was typically used in order to satisfy the need for pseudo first-order conditions in the kinetic analysis. Both ascorbate and $H_2O_2$ showed similar behavior in DNA cleavage reactions, although $H_2O_2$ was slightly more active than ascorbate. Neither ascorbate nor $H_2O_2$ alone, at 250 04 concentration, showed any background DNA cleavage.

Example 5

The dependence of cleavage activity on catalyst concentration showed no saturation behavior indicative of enzyme-like behavior. Consequently, the reaction was considered in terms of the standard rate law shown in equation 3. The initial rate ($V_0$) corresponding to less than 5% conversion was considered as a function of [complex]⁺ (equation 4 and 5).

$$Rate = V = d[DNA]/dt = k_{obs}[complex]_t^m \quad (3)$$

where $k_{obs} = k_n$, [DNA]

$$when\ t=0,\ V_0 = k_{obs}[complex]_0^m \quad (4)$$

$$and\ ln\ V_0 = m\ ln[complex]_0 + ln\ k_{obs} \quad (5)$$

A plot of ln $V_0$ versus ln [[GGH-Cu]⁻]₀ at constant DNA concentration produced a straight line relationship ($R^2$=0.99) (FIG. 27A). The value of m~1 demonstrated the reaction to be first order with respect to the [GGH-Cu]⁻ complex. We have already demonstrated the reaction to be first order with respect to DNA (FIG. 25B), and so the overall reaction is second-order with $k_n = k_2$~39$M^{-1}s^{-1}$.

A plot of ln $V_0$ versus ln [DNA]₀ at constant [GGH-Cu]⁻ concentration (FIG. 3B) yielded a value of m~1 for DNA, again consistent with a first-order reaction for DNA, as shown in FIG. 1B. With the same calculation method, a $k_2$~39 $M^{-1}s^{-1}$ was obtained, consistent with the $k_2$ (39 $M^{-1}s^{-1}$) obtained by plotting ln $V_0$ versus ln [[GGH-Cu]⁻]₀. Similarly, $k_2$~93 $M^{-1}s^{-1}$ was obtained for DNA cleavage by [KGHK-Cu]⁺ (SEQ ID NO: 1) (FIG. 28).

Example 6

Investigation of DNA linearization. Following cleavage, the fraction of full length linear DNA, f(III), is related to the number, n2, of double-strand breaks per molecule given by the first term of a Poisson distribution (equation 1).

$$f(III) = n2\exp(-n2) \quad (1)$$

The sum of single-strand, n1, and double-strand, n2, breaks per molecule (n1+n2) was determined from the fraction f(I) of supercoiled DNA remaining after treatment with the [peptide-Cu] reagent.

$$f(I) = \exp[-(n1+n2)] \quad (2)$$

The Freifelder-Trumbo relation (equation 2) shows that the number of double-strand breaks expected from coincidences of random single-strand breaks is less than 0.01 per molecule, (n1/n2)>100. Consequently, from comparison of the ratio of n1 and n2 (n1/n2) relative to 100, one can determine if the linearization of DNA resulted from random or non-random cleavage. In these studies, both n1 and n2 were calculated by use of equations (1) and (2).

Results.

The complex [KGHK-Cu]⁺ (SEQ ID NO: 1) was observed to produce a well-defined electrophoresis band for linear DNA following limited reaction with supercoiled DNA (FIG. 2). A linear control (form III) was prepared by digesting plasmid DNA with either Eco R I or Bam H I restriction endonuclease. To determine if the observed linearization arose from random or non-random DNA cleavage a standard statistical test was applied. This test assumes a Poisson distribution of strands cuts with calculation of the average number of dsDNA breaks per molecule, n2, from the fraction of linear DNA following strand scission. The total average number of ssDNA and dsDNA breaks (n1+n2) was calculated from the fraction of uncleaved supercoiled DNA.

The Freifelder-Trumbo relationship indicates that more than 100 ssDNA breaks are required to obtain one dsDNA break under completely random conditions. In our experiments, the ratio of n1/n2=14.6±2.9, which is <<100, suggesting a nonrandom cleavage path by [KGHK-Cu]$^+$ (SEQ ID NO: 1) to efficiently form linear DNA.

Example 7

The binding constants for peptides to HCV IRES was determined by fluorescence methods. The sequence of the HCV IRES RNA is: CACGCAGAAAGCGUCUAGC-CAUGGCGUUAGUAUGAGUG (SEQ ID NO: 33). The sequence of the peptide recognition motif is: Y-(D)-RFK. The sequence of the metal binding peptide is: GGH. The sequence of the ligand having a metal binding domain and a recognition domain is GGHGY-(D)-RFK, where (D) indicates a (D) configuration amino acid.

A 10 nM HCV IRES with a fluoroscein label was titrated with increasing concentrations of the ligand, ranging from 5 to 1000 nM in a 50 mM HEPES pH 7.0, 100 mM NaCl, 2 mM MgCl$_2$ to a total volume 200 4. The water used in this experiment was treated with DEPC at 37° C. overnight and autoclaved. HCV IRES RNA was heated at 95° C. for three minutes, and then slowly cooled to the room temperature. The binding event was determined by 96-well fluorescent reader with excitation wavelength at 494 nm and emission wavelength at 520 nm. The result data was plotted as fraction versus peptide concentration (FIG. 29) and then fitted with one site-binding model, where y is equal to API, and x is peptide concentration.

$$y=Bx/(K_d+x)$$

The dissociation constant between HCV IRES and the ligand determined by 96-well fluorescent reader is 5.2 nM.

Example 8

The cleavage of HCV IRES RNA by GGHG-(D) peptide copper complexes was studied. Copper peptide complexes were observed to mediate almost complete cleavage of the HCV IRES RNA with at least one equivalent of complex present. The HCV IRES RNA cleavage reactions by peptide copper complexes, free Cu$^{2+}$, or other peptide metal complexes were carried out at 37° C. in a buffer of 50 mM HEPES pH 7.0, 100 mM NaCl, 2 mM MgCl$_2$. After reactions, 2 μL of loading buffer containing 10% glycerol, 0.05M EDTA, and 6M urea was added into each 10 μL reaction mixture and was then heated at 95° C. for 5 min before loading into 20% acrylamide, 8M urea gel with 0.5×TAE buffer and running voltage around 100 V for overnight. Before cleavage reaction, HCV IRES RNA was heated at 95° C. for 5 min and cooled to room temperature in order to fold into correct structure.

The concentration of RNA in cleavage reaction is 2 μM. The ratio of RNA to metal complexes is 1 to 10. The oxidative cleavage reaction is performed by adding ascorbic acid to a final concentration of 1 mM and a total volume of 10 μL at 37° C. for 24 hours. The result of the cleavage reaction is obtained by running a 20% denaturing polyacrylamide gel. From the result, HCV IRES RNA cleavage by peptide copper complexes only works under oxidative conditions. No hydrolytic product has been observed from the result. While free copper ion is also capable of promoting cleavage under oxidative conditions the efficiency is significantly lower. Moreover, under the reaction conditions used, there is essentially no free copper ion in solutions of the metal-peptide complex.

The time-dependence of cleavage was also examined. The cleavage reaction is carried out under either hydrolytic or oxidative condition. An aliquot of 10 μL reaction mixture contains a final concentration of RNA being 2 μM and 20 μM of peptide copper complex. Each reaction is started at the different time point and stopped at the same time. After the reaction is finished, the result of the reaction is analyzed by running 20% acrylamide gel. The cleavage effect by peptide copper complexes is analyzed by the intensity of the fluorescent image of each band by Biorad GelDoc. The results indicate that the RNA cleavage reaction under oxidative condition was almost completed after 24 hours reaction and is a time dependent reaction (FIG. 30). The time dependence of RNA degradation was then fitted to a first order exponential decay equation. The result of $t_1$ is 9 hour with substrate (RNA) concentration being 2 μM.

Example 9

An in vivo study of RRE RNA Cleavage by Cu-Rev derivative peptide complexes was performed.

General Materials.

The peptides used in this study were purchased from Genemed Synthesis Inc. The DNA oligos used to construct GFP-RRE fusion plasmid were purchased from integrated DNA technologies. Unless stated, all other reagents used in this research were obtained from Sigma chemical Co.

Synthesis and Characterization.

A solution of 2.2 mM peptide in 50 mM Hepes buffer (pH=7.4) was mixed with 2 mM CuCl$_2$ in 50 mM Hepes buffer solution in 1:1 v:v ratio. This yielded a 1.1:1 peptide to copper ratio, and so there was no free Cu$^{2+}$ (aq) ion in the cleavage reaction mixture. The resulting solution was mixed at room temperature for ~30 min, resulting in a stable light reddish-purple solution that displayed a UV-vis spectrum typical of Cu-ATCUN complexes. Samples were maintained at 4° C. and concentrations and stabilities of the Cu-peptide complexes were routinely checked prior to use.

In Vivo Study of RRE RNA Cleavage.

The basic strategy of this study has been described and discussed in Chen et al. The complementary DNA sequences of RRE (5'-AAT TCG GTC TGG GCG CAG CGC AAG CTG ACG GTA CAG GCC GGG C-3' (SEQ ID NO: 34) and 5'-GGC CGC CCG GCC TGT ACC GTC AGC TTG CGC TGC GCC CAG ACC G-3' (SEQ ID NO: 35)) was introduced into the EcoRI/NotI digested pET-21GFP vector. No mutation or frame-shift occurred in the construct was proved by DNA sequencing. *Escherichia coli* strain BL21 (DE3) cells containing pET-21 GFP (as non-specific cleavage control) or pET-21GFP-RRE plasmid were grown to an OD$_{600}$ of around 0.6, and the over-expression was induced with 0.5 mM IPTG at 37° C. incubation. The cell pellets from 500 1 culture were resuspended in resuspension buffer,[3] then lysed with sonicating. After centrifugation (14,000 rpm for 20 min), the cell lysate for each sample was transferred onto 96 well plate and the fluorescence of GFP protein was monitored by a Perkin Elmer LS50B spectrofluorimeter. Excitation and emission wavelengths were set to 390 nm and 510 nm, respectively. The amount of total protein in each cell lysate was measured with Bio-Rad protein assay.

Results.

Cell assays to in vivo screen different Rev peptides and corresponding Cu-Rev peptide complexes. The general strategy of this experiment is shown in FIGS. 33 and 34. Since bacterial cells are permeable to low molecular weight reagents carrying high charge densities, addition of arginine-rich peptides (highly positive charged under physiological condition) can be easily uptaken into E. Coli cells. Basically, once the RRE RNA fused downstream of the GFP mRNA is recognized and cleaved by metal-rev peptide complexes, the expression level of GFP protein will decrease accordingly, which can be monitored by the fluorescence intensity. This is the consequence of down regulation of damaged mRNA expression. With this system, the screening of the RRE cleavage of a group of complexes (FIGS. 34 and 35.) were performed.

The expression level of GFP (GFP-RRE construct) was managed by the fluorescent emission intensity at 510 nm, with $\lambda_{ex}$=390 nm. (FIG. 36). To correct the influence of the total number of cells lysated, the fluorescent emission intensity at 510 nm was divided by the amount of total protein for each sample.

The effect of each rev peptides and Cu-Rev peptide complexes (10 µM final concentration) on the expression of GFP (GFP-RRE construct) was systematically studied and the results of the average of more than triplicate experiments were summarized in (FIG. 37) and corrected with standard deviation. Rev1 and 2 peptide, and corresponding Cu-Rev1 (2) complexes caused the significant decrease of GFP (GFP-RRE construct) expression (around 40% fluorescence intensity/total protein (mg) of control, without any treatment). And this decrease was further enlarged with increasing peptide or Cu-peptide concentrations. However, less effect was observed for Rev3, Rev4, Rev5 and corresponding Cu-peptide complexes and even less at higher concentration.

To distinguish whether the inhibition is caused by RNA cleavage or simply binding effect, Rev peptide alone (without ATCUN, metal binding motif, FIG. 34) was tested in vivo as control. No decrease was observed for Rev peptide alone, on the contrary, slightly increase of GFP (GFP-RRE construct) was observed (FIG. 37). This might suggest that without the ATCUN, Rev peptide still recognize RRE and stabilize the fused mRNA in vivo. On the other hand, with ATCUN, Rev1 and Rev2 picked up a certain metal and cleave RRE RNA target in vivo, resulting in the decrease in translatable mRNA transcript and the expression level of GFP (GFP-RRE construct). This also explained why the expression of GFP (GFP-RRE construct) increased, when the concentrations of inactive (no-cleavage) Rev4 and Rev5 were increased. These results indicate in vivo cleavage of RRE RNA target.

To test the cyto-toxicity of all the Rev peptides and corresponding Cu complexes, the expression of GFP (without RRE) was monitored after the same treatment as described in earlier part. No inhibition effect was observed at 10 µM peptide or complex concentration, which indicates that there is no cyto-toxicity under this condition (FIG. 37).

Time Course of In Vivo Test.

The change of expression of GFP (GFP-RRE construct) with time in samples treated with Rev-1 or Rev1-Cu complex was studied with or without 1 hr pre-incubation. The summarized data of three experiments are shown in FIG. 38. With pre-incubation and extra addition of aliquots of Rev1 or Rev1-Cu showed better inhibition effect than under conditions without pre-incubation and extra addition of aliquots of Rev1 or Rev1-Cu. Adding aliquots of Rev1 or Rev1-Cu hourly keep the concentration of Rev1 or Rev1-Cu at a certain in vivo, which helped to maintain the inhibition effects (FIG. 38). These results reflect the influence of the uptaking and stability of peptide and complex on GFP (GFP-construct) expression.

Example 10

Captopril-cyclam complexes were synthesized and their inhibition/inactivation of ACE was tested.

Synthesis. 1,4,8-Tris(ter-butoxycarbonyl)-1,4,8,11-tetraazacyclotetradecane (1) was synthesized. Synthesis of 1 was performed by reported methods by Dessolin et al. (J. Dessolin, P. Galea, P. Vlieghe, J. Chemann, J. Kraus, J. Med. Chem. 1999, 42, 229-241) with slight modifications. Typically, to a 1 gm of cyclam (5.00 mmol, 1 equiv.) in ice cold $CH_2Cl_2$ (100 mL) was added to 2.0 g of di-tert-butyl dicarbonate (9.00 mmol, 1.8 equiv.). The solution was stirred overnight. After solvent evaporation, the crude pale yellow oil was purified by flash column chromatography (MeOH/$CH_2Cl_2$ 5:95). The first fraction collected was the desired tri-boc protected cyclam (1) as the thick colorless oil (0.75 g, 30% yield). MS (electrospray) 523 (M+Na)$^+$.

(1-(3-mercapto-2-methyl-1-oxoprolyl)-2-(oxoethyl-imino-4-bromo)-proline) (2) was synthesized. Captopril with a brominated arm {(1-(3-mercapto-2-methyl-1-oxoprolyl)-2-(oxoethyl-imino-4-bromo)-proline} was synthesized using dicyclohexylcarbodiimide (DCC) activation of carboxylate in captopril and then coupling with 2-bromo-ethylamine. To a solution (100 mL $CH_2Cl_2$) of 3 g captopril (14 mmol, 1 equiv.) cooled in ice, was added 1.88 g 2-bromo-ethylamine (15.2 mmol, 1.1 equiv.) as free base followed by dropwise addition of 2.84 g DCC (14 mmol, 1 equiv.) over 1 hr. The reaction was stirred for further 6 hr and the precipitated dicyclohexylurea was filtered. Upon solvent evaporation crude product was obtained as a pale yellow solid. The desired product was obtained by flash chromatography ($CH_3CN$, $1^{st}$ fraction) in 30% yield (1.33 g). MS (electrospray) 345 (M+Na)$^+$.

1-{(ethylimino(1-(3-mercapto-2-methyl-1-oxoprolyl)-2-(oxoethyl-imino-4-bromo)-proline)},1,4,8-Tris(ter-butoxycarbonyl)-1,4,8,11-tetraazacyclotetradecane (3) was synthesized. To 1 g boc-protected cyclam 1 (2 mmol, 1 equiv.) dissolved in acetonitrile (100 mL) was added 1 g $Na_2CO_3$ (9.4 mmol ~5 equiv.) and 0.645 g of 2. The reaction was left to stir for 5 days and checked for product formation by TLC. The reaction mixture was then filtered and concentrated. The crude product was purified by flash chromatography (THF, $2^{nd}$ fraction) to obtain pure product 3 in 27% yield (0.40 g) MS (electrospray) 765 (M+Na)$^+$.

1-{(ethylimino(1-(3-mercapto-2-methyl-1-oxoprolyl)-2-(oxoethyl-imino-4-bromo)-proline)},4,8,11-tetraazacyclotetradecane (Capclam) was synthesized. The tri-boc protected product 3 was deprotected by standard methods using 3% TCA in $CH_2Cl_2$. Typically 0.2 g of 3 was treated with 3% TCA in $CH_2Cl_2$ (10 mL) for 2 hr with stirring. The final product Capclam was obtained in almost quantitative yields after a flash column chromatography in $CH_2Cl_2$ and MeOH ($2^{nd}$ fraction) 0.18 g (90%). MS (electrospray) 482 (M+K)'.

Metal complexes of the capclam ligand were (typically 5 mM stock solutions)) formed in 50 mM HEPES (pH 7.4) with 1:1 metal to ligand ratio using the metal chlorides as the source of metal ion. The identity of the complex present and the oxidation state of the metal ion in the complex in the solution was established using mass and UV-vis spectroscopy. The proposed structure is shown in FIG. 39.

Experimental Details for Ace Enzyme Inhibition Assays and Determination of $IC_{50}$ Values for rhACE Inhibitors Using, Mca-Arg-Pro-Pro-Gly-Phe-Ser-Ala-Phe-Lys(Dnp)-OH Substrate (SEQ ID NO: 2):

The rhACE activity was assayed (final volume of 100 µL) at 37° C. in a buffer consisting of 50 mM HEPES containing 300 mM NaCl and 10 µM $ZnCl_2$, pH 7.4 with 10 µM internally quenched fluorogenic peptide substrate, Mca-Arg-Pro-Pro-Gly-Phe-Ser-Ala-Phe-Lys(Dnp)-OH (SEQ ID NO: 2) (R&D Systems Inc.) and 1 nM (13.1 ng) rhACE. Reactions were run in the wells of polystyrene 96-well microplates (Porvair). The increase in the fluorescence upon the cleavage of the peptide was monitored as fluorescence changes (relative fluorescence units/min, RFU/min). Fluorescence changes were measured typically for 30 min using fluorescence microplate reader at 37° C. using PE applications software with excitation and emission wavelengths set at 320 and 405 nm, respectively, with a Perkin Elmer fluorimeter. Optimum substrate concentration was identified by incubating the enzyme with 5 to 50 substrate.

Reaction mixtures (100 µL) contained 50 mM HEPES containing 300 mM NaCl and 10 µM $ZnCl_2$ (pH 7.4), 10 µM substrate and 1 nM (13.1 ng) rhACE. The concentrations of captopril (standard drug), capclam, Co-Capclam were varied from 0 to 1000 nM. Prior to the start of the enzymatic reaction (by addition of substrate) the inhibitors were pre-incubated with the enzyme for 1 hour. Reactions were run in the wells of polystyrene 96-well microplates (Porvair). Fluorescence changes (relative fluorescence units/min, RFU/min) were measured for 30 min using fluorescence microplate reader at 37° C. with excitation and emission wavelengths set at 320 and 405 nm, respectively, using a Perkin Elmer fluorimeter. The background rate determined for samples containing no rhACE was subtracted from all reactions to calculate the initial rates in RFU/min. Initial rate data were plotted as percentage activity relative to uninhibited control reactions versus inhibitor concentration (FIG. 40).

Example 11

The inhibition/inactivation of Thermolysin (TLN) was tested.

Experimental Details for TLN Enzyme Inhibition Assays and Determination of $IC_{50}$ Values for TLN Inhibitors Using, Mca-Arg-Pro-Pro-Gly-Phe-Ser-Ala-Phe-Lys(Dnp)-OH Substrate (SEQ ID NO: 2):

The TLN activity was assayed (final volume of 100 µL) at 37° C. in a buffer consisting of 50 mM HEPES containing 10 mM $CaCl_2$, 5 mM NaCl and 10 $ZnCl_2$, pH 7.4 with 10 µM internally quenched fluorogenic peptide substrate, Mca-Arg-Pro-Pro-Gly-Phe-Ser-Ala-Phe-Lys(Dnp)-OH (SEQ ID NO: 2) (R&D Systems Inc.) and 5 nM TLN enzyme. Reactions were run in the wells of polystyrene 96-well microplates (Porvair). The increase in the fluorescence upon the cleavage of the peptide was monitored as fluorescence changes (relative fluorescence units/min, RFU/min). Fluorescence changes were measured typically for 30 min using fluorescence microplate reader at 37° C. using PE applications software with excitation and emission wavelengths set at 320 and 405 nm, respectively, with a Perkin Elmer fluorimeter. Optimum substrate concentration was identified by incubating the enzyme with 5 to 50 µM substrate (FIG. 41).

Reaction mixtures (100 µL) contained 50 mM HEPES containing 10 mM $CaCl_2$, 5 mM NaCl and 10 µM $ZnCl_2$, pH 7.4 with 10 µM internally quenched fluorogenic peptide substrate, Mca-Arg-Pro-Pro-Gly-Phe-Ser-Ala-Phe-Lys(Dnp)-OH (SEQ ID NO: 2) (R&D Systems Inc.) and 5 nM TLN enzyme. The concentrations of $Cu^{+2}$, $Cu(GGH)^-$, $Cu(KGHK)^+$ (SEQ ID NO: 1), Cu(CGHK) (SEQ ID NO: 3) were varied from 0 to 100 µM. The inhibitors were not pre-incubated with the enzyme as it was not necessary for the enzyme inhibitor complex formation (see figure below, effect of pre-incubation). Reactions were run in the wells of polystyrene 96-well microplates (Porvair). Fluorescence changes (relative fluorescence units/min, RFU/min) were measured for 30 min using fluorescence microplate reader at 37° C. with excitation and emission wavelengths set at 320 and 405 nm, respectively, using a Perkin Elmer fluorimeter. The background rate determined for samples containing no rhACE was subtracted from all reactions to calculate the initial rates in RFU/min. Initial rate data were plotted as percentage activity relative to uninhibited control reactions versus inhibitor concentration (FIGS. 42 and 43).

Time Dependent Deactivation of TLN by CuCGHK (SEQ ID NO: 3):

Enzyme deactivation under oxidative conditions in presence and absence of inhibitor was studied. To obtain a true rate of enzyme deactivation by the inhibitor under oxidative conditions the enzyme incubated with the inhibitor (Final concentrations in well, 5 nM TLN, 1 µM Cu(CGHK) (SEQ ID NO: 3), 0.5 mM Ascorbate (as L-Ascorbic Acid). Aliquots of the reaction mixture were taken at different time intervals and estimated for the residual enzyme activity in a 96-well plate format as per the assay described previously. Initial velocity ($V_o$) obtained in the presence and absence of inhibitor was plotted as a function of time the aliquots were taken and the fitted to the first order rate equation to obtain $k_{obs}$ (FIG. 44).

The present invention should not be considered limited to the specific examples described above, but rather should be understood to cover all aspects of the invention. Various modifications, equivalent processes, as well as numerous structures and devices to which the present invention may be applicable will be readily apparent to those of skill in the art.

It will be obvious to those skilled in the art that various changes may be made without departing from the scope of the invention, which is not to be considered limited to what is described in the specification.

What is claimed is:

1. A ligand comprising at least two separate domains and at least one domain is a metal binding domain and at least one domain is a targeting domain, wherein the ligand has the sequence of GGHTRQARRNRRRRWRERQR (SEQ ID NO: 29).

2. The ligand of claim 1, wherein a metal is bound to the metal binding domain.

3. The ligand of claim 2, wherein the metal comprises copper.

4. The ligand of claim 2, wherein the ligand is a pharmaceutically acceptable basic salt.

5. The ligand of claim 3, wherein the ligand is a pharmaceutically acceptable basic salt.

6. The ligand of claim 2, wherein the ligand is a pharmaceutically acceptable acidic salt.

7. The ligand of claim 3, wherein the ligand is a pharmaceutically acceptable acidic salt.

8. A pharmaceutical composition comprising at least one ligand according to claim 1 and at least one pharmaceutically acceptable excipient.

* * * * *